US012102622B2

(12) United States Patent
Chaudhuri et al.

(10) Patent No.: US 12,102,622 B2
(45) Date of Patent: *Oct. 1, 2024

(54) METHODS FOR OPHTHALMIC DELIVERY OF ROFLUMILAST

(71) Applicant: Iolyx Therapeutics, Inc., Burlingame, CA (US)

(72) Inventors: Bhaskar Chaudhuri, San Jose, CA (US); Hovhannes John Gukasyan, Orange, CA (US)

(73) Assignee: IOLYX THERAPEUTICS, INC., Burlingame, CA (US)

( * ) Notice: Subject to any disclaimer, the term of this patent is extended or adjusted under 35 U.S.C. 154(b) by 86 days.

This patent is subject to a terminal disclaimer.

(21) Appl. No.: 17/668,858

(22) Filed: Feb. 10, 2022

(65) Prior Publication Data

US 2022/0249451 A1 Aug. 11, 2022

Related U.S. Application Data

(60) Provisional application No. 63/261,404, filed on Sep. 20, 2021, provisional application No. 63/148,008, filed on Feb. 10, 2021.

(51) Int. Cl.
*A61K 31/44* (2006.01)
*A61K 9/00* (2006.01)
*A61K 9/10* (2006.01)

(52) U.S. Cl.
CPC ............ *A61K 31/44* (2013.01); *A61K 9/0048* (2013.01); *A61K 9/10* (2013.01)

(58) Field of Classification Search
CPC ..................................................... A61K 31/44
See application file for complete search history.

(56) References Cited

U.S. PATENT DOCUMENTS

| | | | |
|---|---|---|---|
| 5,712,298 A | 1/1998 | Amschler | |
| 6,872,382 B1 | 3/2005 | Gamache et al. | |
| 7,576,069 B2 | 8/2009 | Rieger et al. | |
| 7,605,143 B2 | 10/2009 | Rieger et al. | |
| 8,497,379 B2 | 7/2013 | Choi-Sledeski et al. | |
| 8,614,210 B2 * | 12/2013 | Bhutada | A61K 47/26 514/226.5 |
| 8,663,694 B2 * | 3/2014 | Bruck-Scheffler | A61K 9/1635 424/490 |
| 9,115,133 B2 | 8/2015 | Barawkar et al. | |
| 9,192,623 B2 | 11/2015 | Scott | |
| 2002/0035264 A1 | 3/2002 | Kararli et al. | |
| 2006/0084684 A1 | 4/2006 | Bolle et al. | |
| 2006/0257486 A1 * | 11/2006 | Owen | A61K 31/542 424/486 |
| 2007/0259009 A1 | 11/2007 | Linder | |
| 2008/0255209 A1 | 10/2008 | Klein et al. | |
| 2009/0186923 A1 | 7/2009 | Armer et al. | |
| 2009/0209599 A1 | 8/2009 | Endo et al. | |
| 2011/0086023 A1 | 4/2011 | Lane | |
| 2012/0283252 A1 | 11/2012 | Bhutada et al. | |
| 2015/0125539 A1 | 5/2015 | Popov et al. | |
| 2015/0272936 A1 | 10/2015 | Vakkalanka et al. | |
| 2015/0366890 A1 | 12/2015 | Collins et al. | |
| 2016/0045508 A1 | 2/2016 | Vazquez et al. | |
| 2020/0129461 A1 | 4/2020 | Bannister et al. | |
| 2021/0244718 A1 | 8/2021 | Osborne | |
| 2021/0346661 A1 | 11/2021 | Johnson et al. | |

FOREIGN PATENT DOCUMENTS

| | | | | |
|---|---|---|---|---|
| EP | 1796668 B1 | 9/2008 | | |
| EP | 1906916 B1 | 10/2008 | | |
| EP | 1511516 B1 | 12/2008 | | |
| EP | 2020243 A1 | 2/2009 | | |
| EP | 1511481 B1 | 10/2010 | | |
| EP | 2020243 B1 | 8/2018 | | |
| WO | 9841232 A2 | 9/1998 | | |
| WO | WO2003099278 | * 12/2003 | ............. | A61K 9/107 |
| WO | 2006032675 A1 | 3/2006 | | |

(Continued)

OTHER PUBLICATIONS

Loch, Determination of permeability coefficients of ophthalmic drugsthrough different layers of porcine, rabbit and bovine eyes, European Journal of Pharmaceutical Sciences 47 (2012) 131-138.*
Toropainen Pharmaceutics. Apr. 2021; 13(4): 452.*
International Search Report and the Written Opinion of the International Searching Authority, issued in corresponding International Application No. PCT/US2022/015942, dated Apr. 28, 2022, 7 pages.
Cholkar et al. "Novel Strategies for Anterior Segment Ocular Drug Delivery," Journal of Ocular Pharmacology and Therapeutics, vol. 29, No. 2, Mar. 13, 2013, pp. 106-123.
International Search Report and the Written Opinion of the International Searching Authority, issued in corresponding International Application No. PCT/US2022/076726, dated Nov. 25, 2022, 20 pages.
International Search Report and the Written Opinion of the International Searching Authority, issued in corresponding International Application No. PCT/US2022/076826, dated Dec. 15, 2022, 17 pages.

(Continued)

*Primary Examiner* — Nizal S Chandrakumar
(74) *Attorney, Agent, or Firm* — Rothwell, Figg, Ernst & Manbeck, P.C.

(57) ABSTRACT

Methods for the ophthalmic delivery of roflumilast. The inventors have made the surprising discovery that the administration of pharmaceutical compositions comprising roflumilast to the cornea preferentially delivers the drug laterally through the ocular surface and anterior tissues of the eye. In contrast to the delivery of roflumilast to the skin, which primarily travels transversely through the various tissues of the skin, or many other topical ocular pharmaceutical compositions which travel through the cornea to the aqueous humor, the delivery of drug to the eye to the cornea travels laterally to the ocular surface and anterior tissues of the eye. Such methods can result in elevated levels of the drug in the cornea and other ocular surface and anterior tissues of the eye (e.g., iris-ciliary body, sclera, conjunctiva, and aqueous humor) relative to the interior or posterior tissues of the eye.

18 Claims, 13 Drawing Sheets

(56) References Cited

FOREIGN PATENT DOCUMENTS

| WO | 2006121963 A2 | 11/2006 |
|---|---|---|
| WO | 2015132708 A1 | 9/2015 |
| WO | 2017072131 A1 | 5/2017 |
| WO | 2021100051 A1 | 5/2021 |

OTHER PUBLICATIONS

Sakkas et al., "Phosphodiesterase 4 Inhibitors in Immune-mediated Diseases: Mode of Action, Clinical Applications, Current and Future Perspectives," Current Medicinal Chemistry (2017), 24, 3054-3067.
Tan et al., "Analysis of Th17-associated cytokines in tears of patients with dry eye syndrome," Eye (2014), 28, 608-613.
Liu et al., "Analysis of Th17-associated cytokines and clinical correlations in patients with dry eye disease," PLoS One 12(4) (Apr. 5, 2017), 12 pages.
Riemens et al., "Cytokines in tear fluid of patients with ocular graft-versus-host disease after allogeneic stem cell transplantation," Molecular Vision (2012), 18:797-802.
Rajasagi et al., "The Role of T Cells in Herpes Stromal Keratitis," Frontiers in Immunology, (Mar. 2019), vol. 10, Article 512, 7 pages.
Walscheid et al., "Increased Circulating Proinflammatory T Lymphocytes in Children with Different Forms of Anterior Uveitis: Results from a Pilot Study," Ocul Immunol Inflamm. (2019), 27(5):788-797, 2 pages.
Fung et al., "Local delivery of corticosteroids in clinical ophthalmology: A review," Clin. Experiment Ophthalmol. (2020), 48:366-401.
Kaiko et al., "Immunological decision-making: how does the immune system decide to mount a helper T-cell response?," Immunology, (2007); 123(3): 326-338.
Kim et al., "Tear cytokines and chemokines in patients with Demodex blepharitis," Cytokine, 53, (2011), 94-99.
Allergan, Prescribing Information for PRED FORTE (prednisolone acetate ophthalmic suspension, USP) 1% sterile (2017), 5 pages.
Agarwal et al., "Formulation Considerations for the Management of Dry Eye Disease," Pharmaceutics, 13, 207 (Feb. 3, 2021), 19 pages.
Non-Final Office Action mailed Oct. 26, 2023 in corresponding U.S. Appl. No. 17/948,550, First Named inventor: Richard Graham (19 pages).
Final Office Action mailed Nov. 29, 2023 in corresponding U.S. Appl. No. 17/950,802, First Named inventor: Elizabeth W. Jeffords (10 pages).
Final Office Action mailed Feb. 26, 2024 in corresponding U.S. Appl. No. 17/948,550, First Named Inventor: Richard Graham (12 pages).
Mohr et al., "Gamma irradiation for terminal sterilization of 17Beta-estradiol loaded poly-(D,L-lactide-co-glycolide) microparticles", Journal of Controlled Release 61 (1999) 203-217 (Year: 1999) (15 pages).
Non-Final Office Action mailed May 22, 2024 in corresponding U.S. Appl. No. 17/950,802, First Named Inventor: Elizabeth W. Jeffords ((15 pages).
Non-Final Office Action mailed Jun. 14, 2024 in corresponding U.S. Appl. No. 17/948,550, First Named Inventor: Richard Graham (13 pages).
Wiley A Chambers, MD. Clinical Review #2 for NDA 208144. Feb. 27, 2017. (Year: 2017)(6 pages).
Kalepu et al., "Review. Insoluble drug delivery strategies: review of recent advances and business prospects." Acta Pharmaceutica Sinica B 2015;5(5):442-453 (Year: 2015)(12 pages).

\* cited by examiner

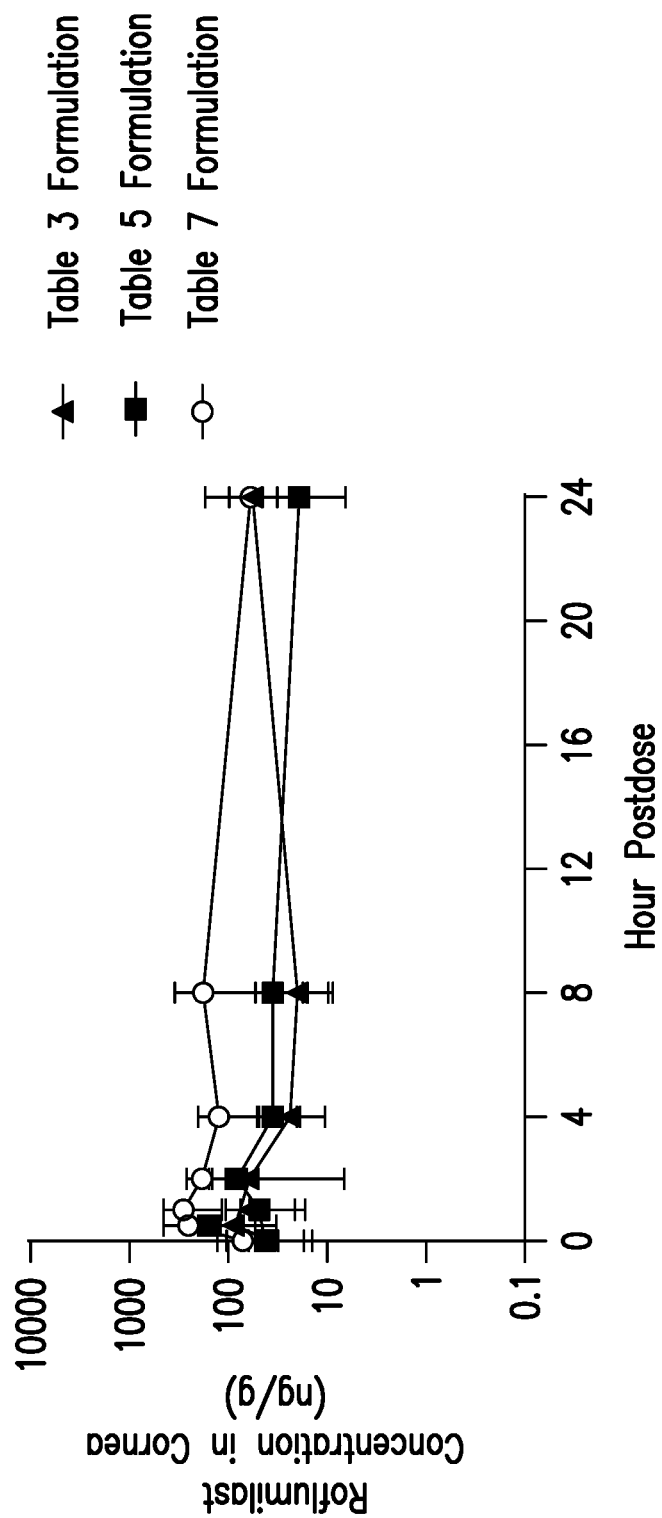

METHODS FOR OPHTHALMIC DELIVERY OF ROFLUMILAST

CROSS REFERENCE TO RELATED APPLICATIONS

The present application claims priority to U.S. Provisional Application No. 63/148,008 filed on Feb. 10, 2021 and U.S. Provisional Application No. 63/261,404 filed on Sep. 20, 2021, the disclosures of which are incorporated herein in their entirety by reference.

FIELD OF THE INVENTION

The present invention relates to methods for the ophthalmic delivery of the phosphodiesterase-4 inhibitor, roflumilast. More specifically, the invention relates to a method for delivering roflumilast such that it is targeted to the ocular surface and anterior tissues of the eye (e.g., the cornea, including the corneal epithelium and corneal endothelium, iris-ciliary body, lens, sclera, conjunctiva, and aqueous humor).

BACKGROUND OF THE INVENTION

Roflumilast is a long-acting inhibitor of phosphodiesterase (PDE) type 4, with anti-inflammatory and potential antineoplastic activities. Roflumilast is known to be suitable as a bronchial therapeutic agent as well as for the treatment of inflammatory disorders. Compositions containing roflumilast are used in human and veterinary medicine and have been proposed for the treatment and prophylaxis of diseases including but not limited to: inflammatory and allergen-induced airway disorders (e.g., bronchitis, asthma, COPD), dermatoses (e.g., proliferative, inflammatory, and allergen induced skin disorders), and generalized inflammations in the gastrointestinal region (Crohn's disease and ulcerative colitis). Oral pharmaceutical compositions of roflumilast are currently marketed under the trademarks Daliresp® (in the United States) and Daxas® (in Europe).

Roflumilast and its synthesis are described in U.S. Pat. No. 5,712,298. It has been recognized that pharmaceutical compounds having phosphodiesterase (PDE)-inhibiting properties, such as roflumilast, are therapeutically effective and useful for treating inflammatory disorders, such as asthma, COPD, Inflammatory Bowel Disease, psoriasis and atopic dermatitis. While the therapeutic effectiveness of oral and dermal pharmaceutical compositions have been studied, there is a need for ophthalmic pharmaceutical compositions of roflumilast suitable for treating inflammatory disorders of the eye.

The delivery of drugs to the eye is very difficult, as pharmaceutical ophthalmic agents must balance sterility, tolerability, convenience, safety, and efficacy. Developing a stable ophthalmic formulation which can be made under sterile conditions while retaining physico-chemical properties, staying within a tight range of pH and inactive ingredients which are tolerable to the eye, and which can be delivered in effective doses to the eye in a manner convenient to frequent patient use is very difficult to achieve. Ophthalmic delivery is typically focused on the ocular surface, the anterior, or posterior segment of the eye. Ocular surface and anterior formulations, often delivered or instilled by the patient as an eyedrop on a one to four times a day schedule, have the additional challenges of needing to address sterility in practical use. Potential variance in temperature and humidity conditions, as well as increased likelihood of being delivered somewhat inexpertly to the proper eye tissue, can cause a variance in delivery volume, placement, and potentially sterility issues, both with the pharmaceutical product and with the delivery device when the drug is delivered in multi-use/multi-dose delivery systems. Patients with long-term inflammatory ocular disease may also have increased or heightened sensitivity to many active and inactive ingredients and preservatives, creating additional challenges of formulation. The majority of the market for anti-inflammatory topical ocular surface treatment today is made up of three classes: anti-biotics, immunosuppressants and steroids; however, many of the pharmaceutical agents within these classes either do not meet the clinical needs of long-term inflammatory disease, or present significant long-term comorbidity and safety issues. As such, there is currently a high unmet need for ophthalmic formulations of an anti-inflammatory agent such as roflumilast capable of delivering effective drug to targeted tissues of the eye in a convenient, tolerable, and safe form. The convenient and efficacious delivery of drug to the eye is even more challenging when optimizing for delivery of drug to the ocular surface and anterior tissues of the eye while minimizing exposure of the posterior tissues. Delivering effective doses to the ocular surface and anterior compartments while avoiding unnecessary exposure in the posterior tissues of the eye to the drug has heretofore not been considered feasible.

There is currently a need for ophthalmic delivery of roflumilast that results in elevated levels of the drug selectively to the ocular surface and anterior tissues of the eye, which are frequently impacted by inflammatory-driven ocular disease.

SUMMARY OF THE INVENTION

The present invention relates to methods for the ophthalmic delivery of roflumilast. As disclosed herein, the inventors of the present invention have made the surprising discovery that the topical administration of pharmaceutical compositions comprising roflumilast to the cornea deliver drug laterally to the ocular surface and anterior tissues. In contrast to the delivery of roflumilast to the skin, which directly travels sequentially through the various tissues of the skin, or the trans-cornea delivery of many current ophthalmic pharmaceutical agents, the delivery of pharmaceutical compositions comprising roflumilast to the cornea travels laterally through the ocular surface tissues, and into the anterior compartment of the eye via the peripheral tissues. Such methods can result in elevated levels of the drug in the cornea, ocular surface, and anterior tissues of the eye (e.g., cornea, conjunctiva, iris-ciliary body, sclera, aqueous humor, and lens) relative to the posterior tissues of the eye (e.g., the vitreous humor and the retina).

In one embodiment, a method for treating a patient having an inflammatory disorder of the eye is provided. The method comprises administering a composition comprising a therapeutically effective amount of roflumilast or a pharmaceutically acceptable salt thereof, to the cornea of said patient. Surprisingly, the roflumilast has been found preferentially to migrate laterally through the ocular surface and anterior tissues, rather than transversely through the cornea. In certain embodiments, the composition is a suspension.

In certain embodiments, the administration produces elevated levels of roflumilast in the cornea of the eye, as well as the peripheral orbital tissues of the conjunctiva, iris-ciliary body, lens, and sclera of the patient relative to the posterior compartments (retina, vitreous humor) of the eye of the patient. The administration can produce elevated levels of roflumilast in a sclera, iris-ciliary body, lens, conjunctiva, and aqueous humor of the eye, as well as the cornea of the patient relative to the posterior tissues of the eye of the patient.

Further, the administration can result in a depot effect in the cornea, conjunctiva, iris-ciliary body, sclera, aqueous humor, or lens of the patient characterized by an increase in the concentration of roflumilast in the eye tissue or component relative to the concentration of roflumilast at an earlier time period following administration.

In another embodiment, a method for delivering roflumilast to the ocular surface or anterior tissues of an eye of a patient is provided. The method comprises administering a composition comprising a therapeutically effective amount of roflumilast, or a pharmaceutically acceptable salt thereof, to the cornea of said patient. The composition delivers roflumilast laterally through the ocular surface and anterior tissues of the eye.

In another embodiment, a method for treating a patient suffering from an ocular surface or anterior eye disorder is provided. The method comprises administering a composition comprising a therapeutically effective amount of roflumilast, or a pharmaceutically acceptable salt thereof, to a cornea of said patient. The composition selectively delivers elevated levels of roflumilast preferentially to the ocular surface or anterior tissues of the eye of the patient relative to the posterior compartments, including the retina, and vitreous humor of the eye of the patient.

BRIEF DESCRIPTION OF THE DRAWINGS

The accompanying drawings, which are incorporated herein and form part of the disclosure, help illustrate various embodiments of the present invention and, together with the description, further serve to describe the invention to enable a person skilled in the pertinent art to make and use the embodiments disclosed herein. The error bars in the drawings are standard deviation values.

FIG. 13 is a graph depicting the concentration of roflumilast in the cornea after five days administration (four days twice a day (BID), fifth day-single dose (QD)) of three different ophthalmic compositions of a 40 µL dose of a 0.1% w/v roflumilast dose in Healthy Dutch Belted Rabbits. The x-axis is time in hours, and the y-axis is concentration (ng/mL) of roflumilast.

DETAILED DESCRIPTION OF THE INVENTION

Figure 1:
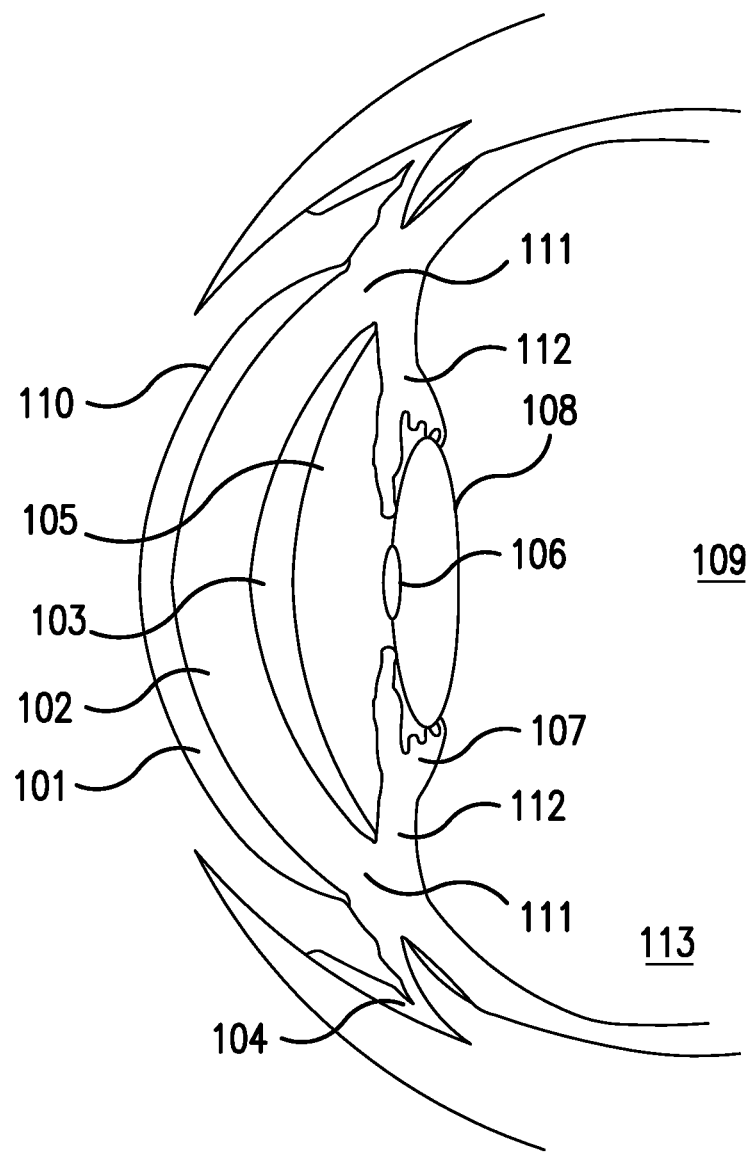
FIG. 1 is a schematic diagram of an eye of a subject for purposes of illustrating the movement of roflumilast according to certain embodiments of the present invention.

It is to be understood that the invention is not limited to the particular methodology, protocols, and reagents described herein as these may vary. It is also to be understood that the terminology used herein is for the purpose of describing particular embodiments only and is not intended to limit the scope of the present invention which will be limited only by the appended claims. Unless defined otherwise, all technical and scientific terms used herein have the same meanings as commonly understood by one of ordinary skill in the art to which this invention belongs.

All publications, patents and patent applications cited herein are hereby incorporated by reference in their entirety unless otherwise stated. Where the same term is defined in a publication, patent, or patent application and the present disclosure incorporated herein by reference, the definition in the present disclosure represents a controlling definition. For publications, patents and patent applications referenced to describe a particular type of compound, chemistry, etc., the portion relating to such compounds, chemistry, etc. is the portion of the literature incorporated herein by reference.

Note that as used herein, the singular forms "a," "an," and "the" include plural referents unless the context clearly dictates otherwise. Thus, for example, "active ingredient" includes a single ingredient and two or more different ingredients.

The term "about" when used in connection with a numerical value is meant to encompass numerical values within a range having a lower limit that is 5% smaller than the indicated numerical value and having an upper limit that is 5% larger than the indicated numerical value.

The terms "anterior tissue" or "anterior compartment" of the eye refer to a tissue or compartment of the eye located behind the ocular surface toward the front of the eye, including the iris-ciliary body, aqueous humor, cornea endothelium, and the lens.

The term "effective" refers to an amount of a compound, agent, substance, formulation or composition that is of sufficient quantity to result in a decrease in severity of disease symptoms, an increase in frequency and duration of disease symptom-free periods, or a prevention of impairment or disability due to the disease affliction. The amount may be as a single dose or according to a multiple dose regimen, alone or in combination with other compounds, agents or substances. One of ordinary skill in the art would be able to determine such amounts based on such factors as a subject's size, the severity of a subject's symptoms, and the particular composition or route of administration selected.

The term "eye disorder," "eye condition," or "ocular disorder," refer to diseases/conditions of the eye(s) that can be sight threatening, lead to eye discomfort, and may signal systemic health problems. The term "ocular surface disease" or "ocular surface disorder" refers to all diseases/conditions that affect an ocular surface site such as the pre-cornea and exterior cornea (including the cornea epithelium and stroma), conjunctiva, sclera (those portions not in the posterior of the eye), eyelids, lacrimal and Meibomian glands, and the interconnecting nerves. The term "anterior eye disease" or "anterior eye disorder" refers to all diseases/conditions that affect an anterior ocular site such as the interior cornea (including the corneal endothelium), the aqueous humor, and the anterior surface of the lens.

The term "ocular surface" refers to a surface located on the front of the eye, including the pre-cornea, cornea, conjunctiva, sclera (those portions not in the posterior), and tissues of the eyelid.

"Pharmaceutically acceptable" means generally safe for administration to humans or animals. Preferably, a pharmaceutically acceptable component is one that has been approved by a regulatory agency of the Federal or a state government or listed in the U.S. Pharmacopeia, published by the United States Pharmacopeial Convention, Inc., Rockville Md., or other generally recognized pharmacopeia for use in animals, and more particularly in humans.

A "pharmaceutical composition" according to the invention may be present in the form of a composition, wherein the different active ingredients and diluents and/or carriers are admixed with each other, or may take the form of a combined preparation, where the active ingredients are present in partially or totally distinct form. An example for such a combination or combined preparation is a kit-of-parts.

The terms "posterior tissue" or "posterior compartment" of the eye refer to a tissue or compartment of the eye located toward the back of the eye, posterior to the anterior compartment, including the posterior lens, the vitreous humor, choroid, RPE, and the retina.

The term "roflumilast" as used in this application refers to roflumilast, prodrugs, and salts thereof unless specified otherwise or unless it is clear in context that reference is to roflumilast itself.

As used herein, the terms "subject" "or patient" most preferably refers to a human being. The terms "subject" or "patient" may include any mammal that may benefit from the compounds described herein.

A "therapeutic amount" or "therapeutically effective amount" is an amount of a therapeutic agent sufficient to achieve the intended purpose. The effective amount of a given therapeutic agent will vary with factors such as the nature of the agent, the route of administration, the size of the subject to receive the therapeutic agent, and the purpose of the administration. The effective amount in each individual case may be determined empirically by a skilled artisan according to established methods in the art.

As used herein, "treat," "treating," or "treatment" of a disease or disorder means accomplishing one or more of the following: (a) reducing the severity and/or duration of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

The present invention relates to methods for the ophthalmic delivery of roflumilast. As disclosed herein, the inventors of the present invention have made the surprising discovery that the administration of pharmaceutical compositions comprising roflumilast to the cornea results in drug delivery that preferentially travels laterally through the eye. In contrast to the delivery of roflumilast to the skin, which primarily travels transversely through the various tissues of the skin, and many ocular agents, which travel transversely through the cornea, the delivery of the present invention to the eye to the cornea travels laterally toward the ocular surface and anterior tissues of the eye. Such methods can result in elevated levels of the drug in the cornea and ocular surface and anterior tissues of the eye relative to the posterior of the eye.

Roflumilast is a compound of the formula (I):

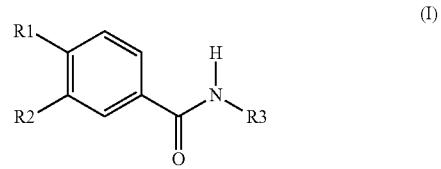

wherein R1 is difluoromethoxy, R2 is cyclopropylmethoxy and R3 is 3,5-dichloropyrid-4-yl.

Roflumilast has the chemical name N-(3,5-dichloropyrid-4-yl)-3-cyclopropylmethoxy-4-difluoromethoxybenzamide. The N-oxide of roflumilast has the chemical name 3-cyclopropylmethoxy-4-difluoromethoxy-N-(3,5-dichloropyrid-4-yl 1-oxide)benzamide. Roflumilast and its synthesis, the use of roflumilast as a phosphodiesterase (PDE) 4 inhibitor, and roflumilast formulations, were described in U.S. Pat. No. 5,712,298, which is incorporated herein by reference.

In the present invention, roflumilast is administered to an eye of a patient. A pharmaceutical composition comprising roflumilast can be administered in the form of a conventional ophthalmological pharmaceutical preparation, as would be known by a person of ordinary skill in the art. For example, the ophthalmological pharmaceutical preparation can be in the form of an ophthalmological pharmaceutical suspension or solution. In certain embodiments, the ophthalmological pharmaceutical preparation can be an ointment or other local delivery to the ocular surface.

The roflumilast can be administered to the eye of a patient having an eye disorder or eye condition. The methods disclosed herein deliver elevated levels of roflumilast to the cornea of the patient. Administration using the disclosed methods produces elevated levels of roflumilast in the cornea, including the cornea, the sclera, conjunctiva, the iris-ciliary body, and eventually the aqueous humor of the eye and the lens of the patient relative to the posterior tissues of the eye of the patient. Further, the administration can result in a depot effect in one or more tissues or components of the tissues of the eye, such as the cornea, conjunctiva, iris-ciliary body, sclera, or aqueous humor. A depot effect is characterized by an increase in the concentration of roflumilast in the tissue or component of the eye relative to the concentration of roflumilast in the tissue or component of the eye at an earlier time period following administration. The methods disclosed herein can achieve therapeutic amounts of roflumilast in the ocular surface and anterior compartment, including for example, the cornea, aqueous humor, iris-ciliary body, conjunctiva, and sclera for a sustained period of time. For example, in certain embodiments, the methods disclosed herein can result in a therapeutic amount for at least 4 hours, at least 8 hours, at least 12 hours, at least 16 hours, at least 20 hours, at least 24 hours, or longer.

FIG. 1 is a schematic diagram of the front half of the eye of a subject for purposes of illustrating the movement of roflumilast through the eye according to certain embodiments of the present invention. In FIG. 1, the corneal epithelium 101, corneal stroma 102, corneal endothelium 103, conjunctiva 104, aqueous humor 105, pupil 106, iris-ciliary body 107, lens 108, and posterior compartment 109 are illustrated. In certain embodiments, roflumilast is administered on the surface of the cornea 110 via an ophthalmic pharmaceutical composition (e.g., a suspension). Administration of an ocular suspension instills drug on an ocular surface 110, which enables migration of the drug from the ocular surface 110 to transitional tissues between ocular surface and anterior compartment 111 and then to the anterior compartment 112. That is, following administration of an ophthalmic pharmaceutical composition of roflumilast, the drug migrates from 110 to 111 to 112. Without being bound by theory, the unique lipophilic nature of the compound and the epithelial cornea facilitate the ocular drug path and the longer ocular surface residence, preventing a more direct transit from 110 to 112 through the corneal stroma and endothelium, which is the pathway used by many other ocular therapeutics. In certain embodiments, limited amounts of roflumilast migrate to the posterior compartments of the eye 113.

Figure 2:
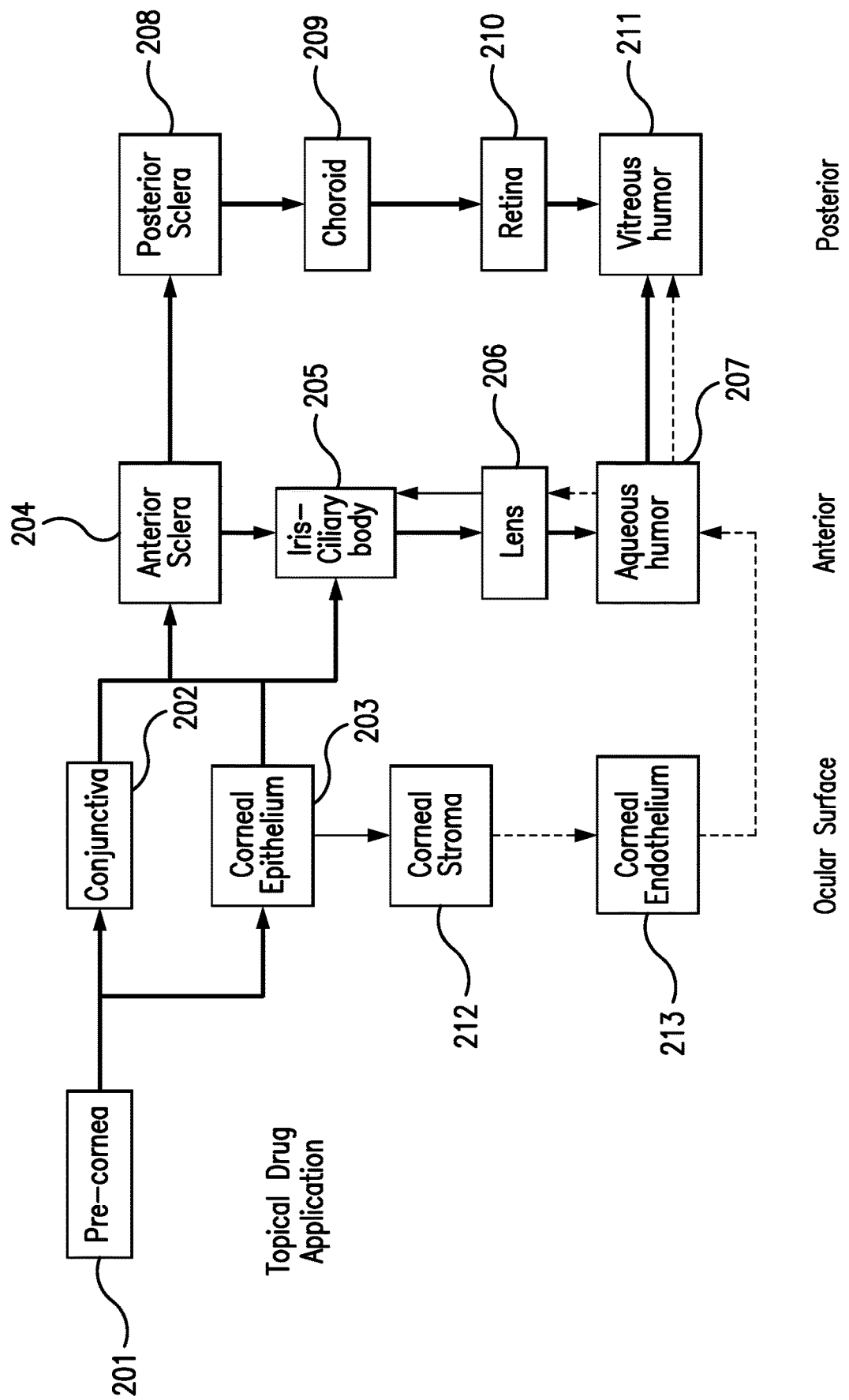
FIG. 2 is a flow diagram showing various compartments of the eye and potential pathways for ophthalmologic delivery of a pharmaceutical ingredient.

FIG. 2 is a flow diagram showing various compartments of the eye and potential pathways for ophthalmologic delivery of a pharmaceutical ingredient. The various compartments of the eye, including the pre-cornea where topical drug is instilled 201, conjunctiva 202, corneal epithelium 203, anterior sclera 204, iris-ciliary body 205, lens 206, aqueous humor 207, posterior sclera 208, choroid 209, retina 210, vitreous humor 211, corneal stroma 212, and corneal endothelium 213, are represented by boxes in a flow diagram. The arrows connecting the boxes depict potential pathways for drug migration. In certain embodiments, shown in the thick dark arrows, an ophthalmic pharmaceutical composition of roflumilast is administered on the surface of the cornea 201 via an ophthalmic pharmaceutical composition (e.g., a suspension or ointment). Roflumilast can migrate from the cornea 201 to the conjunctiva 202 and corneal epithelium 203, traveling then laterally to the transitional/anterior tissues of the anterior sclera 204 and the iris-ciliary body 205 and then further into the anterior compartment and the lens 206 and aqueous humor 207, and eventually in a reduced volume into the posterior compartment of the eye of a patient. In contrast, as marked by the thinner dotted line, many other ocular therapeutics deliver drug from the pre-cornea 201 to the corneal epithelium 203 through the corneal stroma 212 and corneal endothelium 213 to the aqueous humor 207 and to the iris-ciliary body 205 and lens 206. Systemic exposure would typically occur via the aqueous humor 207 and vascular organs in either method. The methods of administration disclosed herein can result in a favorable pharmacokinetic profile, which allow for treatment of ocular surface and anterior tissue disorders.

The methods of the present invention can be used to treat ocular surface or anterior diseases, which require long-term pharmacological treatment without the need for invasive techniques, which would otherwise be treated with existing anti-inflammatory agents, which have various short- and long-term side effects, particularly when used over an =extended period. These ocular surface and anterior diseases include: post-operative inflammation, post-corneal refractive surgery haze, dry eye syndrome, evaporative dry eye disease, ocular graft vs. host disease, ocular complications of Sjogren's disease, inflammatory dry eye disease, ocular rosacea, allergic conjunctivitis or keratoconjunctivitis, atopic keratoconjunctivitis, phlyctenulosis, staphylococcal hypersensitivity, Mooren's ulcer, endotheleitis, vernal keratoconjunctivitis, superior limbic keratoconjunctivitis, post-operative full or partial thickness corneal transplantation, keratitis, herpetic keratitis including herpetic stromal keratitis/herpetic blepharitis or conjunctivitis, zoster related inflammation, inflammation secondary to other infectious agents, inflammation secondary to ocular chemical burns, uveitis including uveitis of juvenile idiopathic arthritis, seborrheic or other forms of blepharitis, limbal stem cell deficiency, Meibomian gland dysfunction, episcleritis, pingueculitis, and pterygia. The ocular surface or anterior eye disorders treatable by the methods described herein can be acute or chronic.

In certain embodiments, the method is used to treat a patient having an inflammatory disorder of the eye. In certain embodiments, the inflammatory disorder is selected from the group consisting of dry eye, herpetic ocular disease, blepharitis, or uveitis.

In the present invention, the patient is administered an ophthalmic pharmaceutical composition. The ophthalmic pharmaceutical composition can include roflumilast as a free base or a pharmaceutically acceptable salt. Exemplary salts of roflumilast are salt described in paragraphs [0012] and [0013] of U.S. Patent Application Publication No. US 2006/0084684, the disclosure of which is incorporated herein by reference. In certain embodiments, the ophthalmic pharmaceutical composition can include an active metabolite or prodrug of roflumilast or a salt thereof.

The ophthalmic pharmaceutical composition can be formulated into such preparations utilizing a number of well-known and widely-used methods to those of ordinary skill in the art. In certain embodiments, the ophthalmic pharmaceutical composition is administered topically, directly to the eye, in the form of a suspension, solution, eye drops, eye ointments, gels, a spray, or an adsorbent contact lens. In preferred embodiments, the pharmaceutical composition is a suspension, wherein the active ingredient (i.e., roflumilast) is suspended in a pharmaceutical carrier and/or excipients. In certain embodiments, the ophthalmic pharmaceutical composition can include one or more of a buffer, viscosity agent, surfactant, stabilizer, preservative, wetting agent, diluting agent, pH adjuster, tonicity agent, stabilizing agent, or absorption enhancer.

In certain embodiments, the ophthalmic pharmaceutical composition includes an amount of roflumilast that can range from about 0.01% w/v to about 7.5% w/v, or from about 0.01% w/v to about 5% w/v, or from about 0.1% w/v to about 3% w/v. Exemplary ranges are from about 0.01% w/v to about 5% w/v, or from about 0.01% w/v to about 3% w/v, or from about 0.1% w/v to about 3% w/v, or from about 0.3% w/v to about 3.0% w/v. For example, the ophthalmic pharmaceutical comprises any of the following w/v percents of roflumilast: 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 7%, 1.8%, 1.9%, 1.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, etc.

In certain embodiments, the ophthalmic pharmaceutical composition includes a carbomer, such as a carbomer copolymer Type A or a carbomer copolymer Type B including those marketed under the trade name Carbopol® by Lubrizol®. In certain embodiments, the ophthalmic pharmaceutical composition includes a carboxymethylcellulose or salt thereof, such as carboxymethylcellulose sodium. In certain embodiments, the ophthalmic pharmaceutical composition includes methacrylate derivatives or ethacrylate derivatives such as those marketed under the trade name Eudragit.

In certain embodiments, the viscosity agent is at least one selected from the group consisting of hydroxypropyl methylcellulose (HPMC), hydroxyethylcellulose (HEC), polyvinylpyrrolidone or povidone, carboxymethyl cellulose, hypromellose, methylcellulose, or polyvinyl alcohol (PVA). In certain embodiments, the viscosity agent is a dextran or gelatin. In addition, the viscosity agent can include a carbomer in certain embodiments, such as a carbomer copolymer Type A or a carbomer copolymer Type B including those marketed under the trade name Carbopol® by Lubrizol®. In certain embodiments, the ophthalmic pharmaceutical formulation can comprise a viscosity agent in a range from about 0.1% w/v to about 5.0% w/v, or from about 0.1% w/v to about 4.0% w/v, or from about 0.1% w/v to about 3.0% w/v, or from about 0.1% w/v to about 2.0% w/v, or from about 0.1% to about 1.0% w/v, or from about 0.1% to about 0.5% w/v. For example, the ophthalmic pharmaceutical comprises any of the following w/v percents of a viscosity agent: 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 7%, 1.8%, 1.9%, 1.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, etc.

In certain embodiments, the surfactant is at least one selected from the group consisting of polysorbates (including, polysorbate 20, polysorbate 40, polysorbate 60, and polysorbate 80) and tyloxapol. In certain embodiments, the ophthalmic pharmaceutical formulation can comprise a surfactant in a range from about 0.05% w/v to about 3.0% w/v, or from about 0.05% w/v to about 2.0% w/v, or from about 0.05% to about 1.0% w/v, or from about 0.1% to about 0.5% w/v. For example, the ophthalmic pharmaceutical comprises any of the following w/v percents of a surfactant: 0.05%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 7%, 1.8%, 1.9%, 1.0%, 2.1%, 2.2%, 2.3%, 2.4%, 2.5%, 2.6%, 2.7%, 2.8%, 2.9%, 3.0%, etc.

In certain embodiments, the buffer is at least one selected from the group consisting of citrate, phosphate, Tris-HCl (Tris), acetate, and borate buffers. In certain embodiments, the ophthalmic pharmaceutical formulation can comprise a buffer in a range from about 0.5% w/v to about 7.5% w/v, or from about 0.5% w/v to about 5.0% w/v, or from about 0.5% to about 3.0% w/v, or from about 0.5% w/v to about 2.0% w/v, or from about 0.5% to about 1.0% w/v. For example, the ophthalmic pharmaceutical comprises any of the following w/v percents of a buffer: 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 7%, 1.8%, 1.9%, 1.0%, 2.1%, 2.2%, 2.3%, 2.4%, 2.5%, 2.6%, 2.7%, 2.8%, 2.9%, 3.0%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, etc.

In certain embodiments, the ophthalmic pharmaceutical composition comprises a therapeutically effective amount of roflumilast, a viscosity agent comprising hydroxypropyl methylcellulose, a surfactant, and a buffer. In certain embodiments, the surfactant is a polysorbate. In certain embodiments, the buffer is a phosphate and citrate buffer. In certain embodiments, the pharmaceutical composition is a suspension. In preferred embodiments, the pharmaceutical composition has a particle size distribution characterized by a d90 value of from about 5 μm to about 25 μm, or more preferably, less than or equal to about 15 μm.

In certain embodiments, the ophthalmic pharmaceutical composition comprises a therapeutically effective amount of roflumilast, a viscosity agent comprising hydroxyethyl cellulose, a surfactant, and a buffer. In certain embodiments, the surfactant is a polysorbate. In certain embodiments, the buffer is a phosphate and citrate buffer. In certain embodiments, the pharmaceutical composition is a suspension. In preferred embodiments, the pharmaceutical composition has a particle size distribution characterized by a d90 value of from about 5 μm to about 25 μm, or more preferably, less than or equal to about 15 μm.

In certain embodiments, the ophthalmic pharmaceutical composition comprises a therapeutically effective amount of roflumilast, a viscosity agent comprising polyvinylpyrrolidone, a surfactant, and a buffer. In certain embodiments, the surfactant is a tyloxapol. In certain embodiments, the buffer is a phosphate and citrate buffer. In certain embodiments, the pharmaceutical composition is a suspension. In preferred embodiments, the pharmaceutical composition has a particle size distribution characterized by a d90 value of from about 5 µm to about 25 µm, or more preferably, less than or equal to about 15 µm.

In certain embodiments, the ophthalmic pharmaceutical composition comprises a therapeutically effective amount of roflumilast, a viscosity agent comprising carboxymethyl cellulose, a surfactant, and a buffer. In certain embodiments, the surfactant is a polysorbate. In certain embodiments, the buffer is a phosphate and citrate buffer. In certain embodiments, the pharmaceutical composition is a suspension. In preferred embodiments, the pharmaceutical composition has a particle size distribution characterized by a d90 value of from about 5 µm to about 25 µm, or more preferably, less than or equal to about 15 µm.

In certain embodiments, the ophthalmic pharmaceutical formulation is an ointment. The ointment can include inactive ingredients selected from the group consisting of petrolatum, mineral oil. In such embodiments, the ophthalmic pharmaceutical formulation can comprise a therapeutically effective amount of roflumilast, petrolatum, and mineral oil. In certain embodiments, the composition comprises from about 0.1% w/v to about 3.0% w/v, or from about 0.1% w/v to about 2.0% w/v, or from about 0.1% to about 1.0% w/v of roflumilast. In certain embodiments, the composition comprises from about 75% to about 85% w/w of petrolatum, or more preferably from about 75% to about 80% w/w of petrolatum. In certain embodiments, the composition comprises from about 15% to about 25% w/w mineral oil, or more preferably from about 15% to about 20% w/w of mineral oil. The ointment can provide benefits relative to suspensions, including for example, increasing contact time and increasing the soluble drug concentration in the dosing system, which can be important for a water-insoluble drug like roflumilast.

In preferred embodiments, the pH of the ophthalmic pharmaceutical composition is between about 5.6 and about 8.3, between about 6.0 to about 8.0, between about 7.0 to about 8.0, between about 6.0 to about 6.7, between about 6.2 to about 6.7, or about 6.3 to about 6.6. It has been identified that roflumilast undergoes hydrolysis in certain ophthalmic pharmaceutical compositions and under certain standard sterile manufacturing processes. In certain embodiments, the pH of the ophthalmic pharmaceutical composition is between about 6.0 and about 6.7 to reduce the rate of hydrolysis of roflumilast. In preferred embodiments, the pH of the ophthalmic pharmaceutical composition is between about 6.2 and about 6.7, and more preferably between about 6.3 to about 6.6. In preferred embodiments, the osmolality of the ophthalmic pharmaceutical composition is about 270 mOsm/kg to 330 mOsm/kg, more preferably about 270 mOsm/kg to about 300 mOsm/kg, and even more preferably 270 mOsm/kg to 280 mOsm/kg.

The ophthalmic pharmaceutical compositions can be stable and exhibit a particle size distribution suitable for ophthalmic delivery. The particle size of suspensions can be assessed using laser diffraction methods. Laser diffraction is recognized by standards and guidance agencies including ISO and ASTM and is widely used to determine particle size distributions. In conducting the assessment, the sample is passed through a laser beam, which results in laser light scattered at a range of angles. Detectors placed at fixed angles measure the intensity of light scattered at that position. A mathematical model is then applied to generate a particle size distribution.

In particle size determinations, the median value is defined as the value where half of the population resides above this point, and half resides below this point. For particle size distributions the median is called the D50. The D50 is the size that splits the distribution with half above and half below this diameter. The distribution width may also be characterized by citing one, two or three values on the x-axis, typically some combination of the D10, D50, and D90. The D50 (or the median), as discussed above, refers to the diameter wherein half of the population lies below this value. Similarly, 90 percent of the distribution lies below the D90, and 10 percent of the population lies below the D10.

In certain embodiments of the present invention, the ophthalmic pharmaceutical composition exhibits a particle size distribution characterized by a d90 value of less than or equal to about 50 µm prior to preferential processing. In certain embodiments, the ophthalmic pharmaceutical composition exhibits a particle size distribution characterized by a d90 value of from about 5 µm to about 25 µm. In certain embodiments, the pharmaceutical compositions exhibits a particle size distribution characterized by a d90 value of from about 5 µm to about 15 µm. In preferred embodiments, the pharmaceutical compositions exhibit a particle size distribution characterized by a d90 value of less than or equal to 15 µm.

In certain embodiments, the pharmaceutical composition is administered as a regimen, such as at regular intervals. For example, a pharmaceutical composition can be administered once daily, twice daily, thrice daily, four times daily, once per week, twice per week, three times per week, or four times per week. In certain embodiments, the pharmaceutical composition can be administered as part of a maintenance dose or titrating dose regimen. The pharmaceutical composition can be administered for a prescribed period of time or indefinitely. For example, a pharmaceutical composition can be administered for a period of about two days to at least about six weeks, or until an improvement in the eye condition or disease is observed. Exemplary periods of time for the treatment regimen include one week, two weeks, one month, six weeks, two months, three months, four months, five months, six months, seven months, eight months, nine months, or one year. In preferred embodiments, the topical pharmaceutical composition is administered twice or thrice daily for a period of at least 3 months, 4 months, 5 months, 6 months, 1 year, etc. In certain embodiments, the exemplary period of time for the treatment can be indefinite.

The following examples illustrate certain embodiments of the invention without limitation.

EXAMPLES

While various embodiments have been described above, it should be understood that they have been presented by way of example only, and not limitation. Thus, the breadth and scope of the present disclosure should not be limited by any of the above-described exemplary embodiments. Moreover, any combination of the above-described elements in all possible variations thereof is encompassed by the disclosure unless otherwise indicated herein or otherwise clearly contradicted by context.

Example 1

Ophthalmic pharmaceutical compositions comprising roflumilast were prepared. The two suspension formulations set forth in Tables 1 and 2 were prepared.

TABLE 1

Exemplary Suspension of Roflumilast

| Ingredient | % w/v |
|---|---|
| Roflumilast | 0.10% w/v |
| Tyloxapol | 0.05% w/v |
| Carbopol 974B (Lubrizol) | 0.2% w/v |
| Glycerin | 2.0% w/v |
| Sodium chloride | 0.05% w/v |
| 1N NaOH/HCl | pH adjustment to 7.4 +/− 0.2 |
| Water for injection | q.s. ad 1.0 mL |

TABLE 2

Exemplary Suspension of Roflumilast

| Ingredient | % w/v |
|---|---|
| Roflumilast | 0.10% w/v |
| Tyloxapol | 0.05% w/v |
| Carbopol 974B (Lubrizol) | 0.25% w/v |
| Propylene glycol | 1.4 w/v % |
| Sodium chloride | 0.3% w/v |
| Mannitol | 0.3% w/v |
| 1N NaOH/HCl | pH adjustment to 7.4 +/− 0.2 |
| Water for injection | q.s. ad 1.0 mL |

Example 2

An ocular five-day pharmacokinetic preclinical study was conducted in Dutch Belted Rabbits (n=36) with three arms (cohort 1: n=3, no active therapy; cohort 2: n=15, 1-day dosing, cohort 3: n=18, 5-day dosing). For the 1-day dosing a single dose was given, for the 5-day dosing, BID dosing was performed for days 1-4, with a single dose on day 5. Each dose consisted of an ophthalmic suspension comprising 25 µL of 0.1% roflumilast applied to both eyes of the subjects. The suspension set forth in Table 2 was used for Example 2. Plasma samples were taken on days 1 and 5. Plasma concentrations plus concentrations in other tissues and components of the eye, including the cornea (Cr), aqueous humor (AqH), iris-ciliary body (ICB), lens, retina-choroid plexus (retina), vitreous humor (Vit), and sclera (Sclr), were analyzed at various time points.

Figure 3:
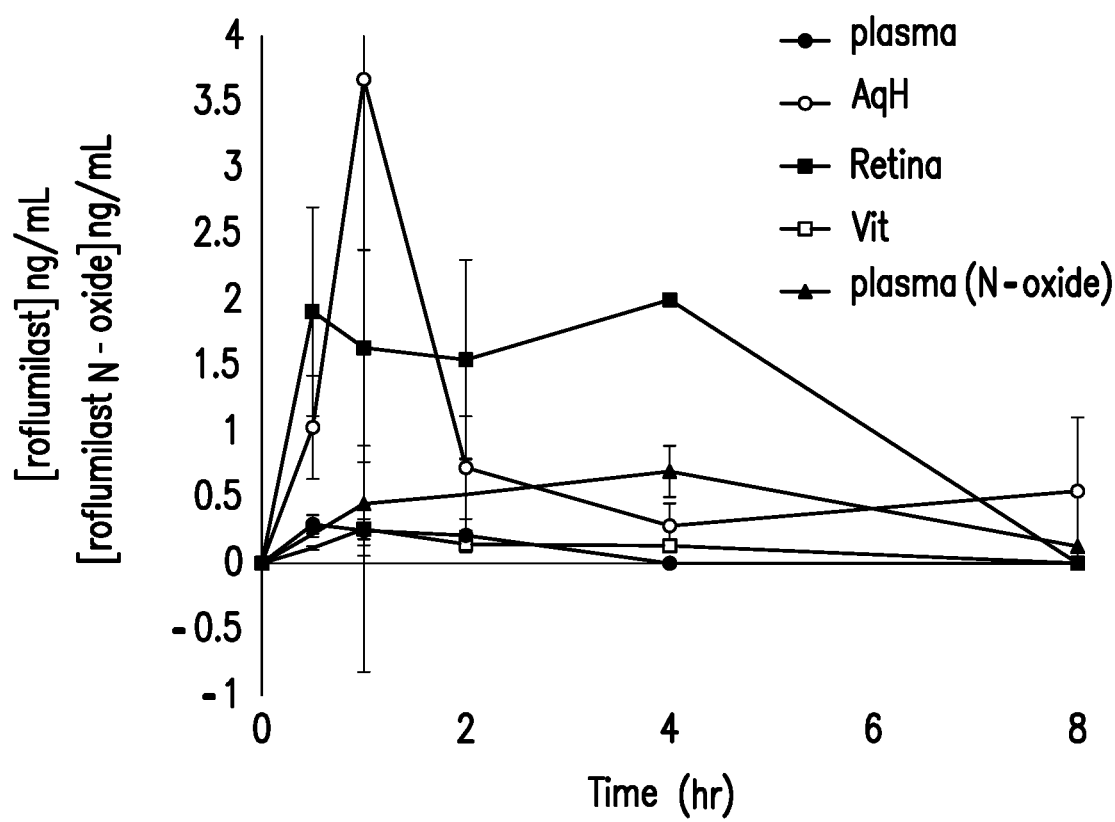
FIG. 3 is a graph depicting the concentration of roflumilast or roflumilast n-oxide in various components of the eye following administration of a single 25 µL dose of a 0.1% w/v roflumilast dose in Healthy Dutch Belted Rabbits. The x-axis is time in hours, and the y-axis is concentration (ng/mL) of roflumilast or roflumilast n-oxide.
Figure 4:
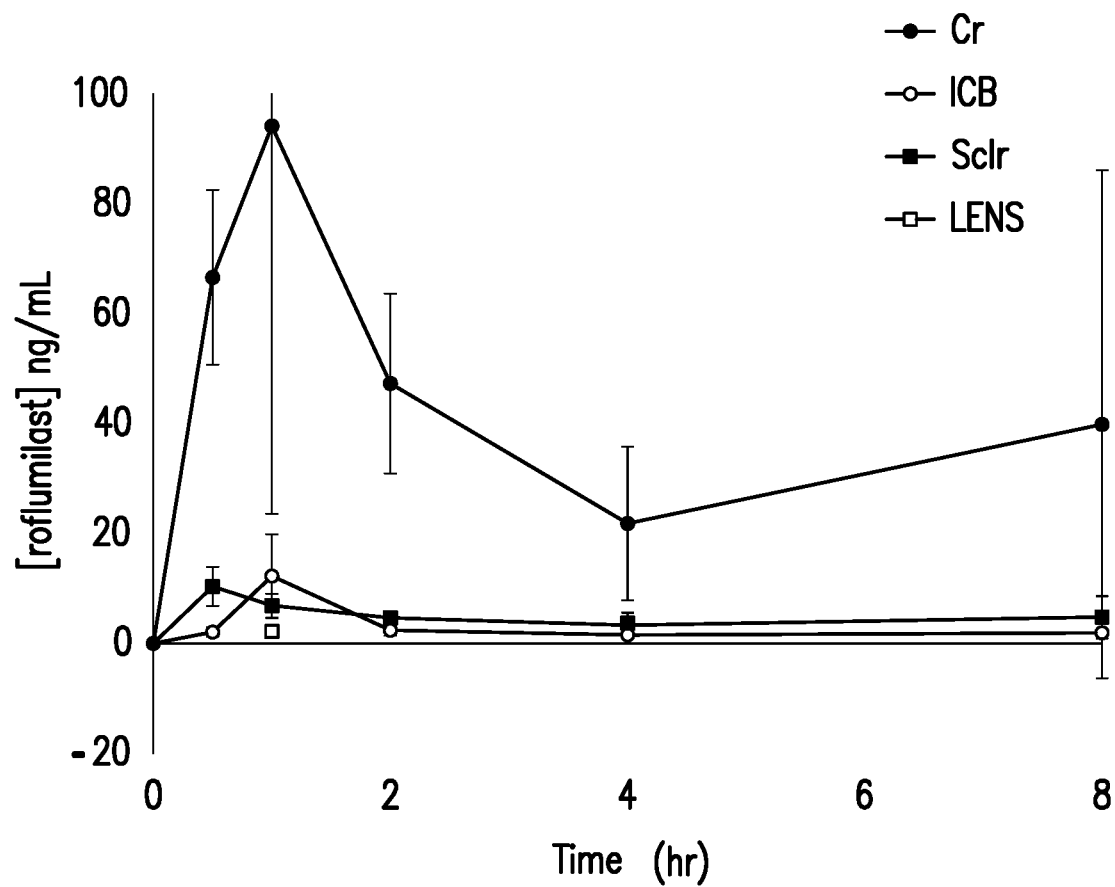
FIG. 4 is a graph depicting the concentration of roflumilast in various components of the eye following administration of a single 25 µL dose of a 0.1% w/v roflumilast dose in Healthy Dutch Belted Rabbits. The x-axis is time in hours, and the y-axis is concentration (ng/mL) of roflumilast.

The results of the study in Dutch Belted Rabbits are set forth in FIGS. 3-8. FIGS. 3 and 4 show the concentration of roflumilast and roflumilast n-oxide in the plasma and various components of the eye on day 1 of the study following a single dose was administered to the subjects. FIG. 3 shows the concentration of roflumilast or roflumilast n-oxide in the plasma, aqueous humor, retina-choroid plexus, and vitreous. FIG. 4 shows the concentration of roflumilast in the cornea, iris-ciliary body, sclera, and lens (after 1 hour). In both FIGS. 3 and 4, the x-axis is time in hours, and the y-axis is concentration (ng/mL) of roflumilast or roflumilast n-oxide.

FIGS. 3 and 4 show that there is high variability of the drug in the cornea over time. In the cornea, sclera, iris-ciliary body, and aqueous humor, there is an elevated rise in levels of roflumilast following administration followed by a decrease in levels. Surprisingly, the results indicate that the drug is reaching the ocular surface and anterior areas of the eye, including for example, the iris-ciliary body, sclera, and aqueous humor. The results further indicate that the drug is moving laterally through the eye. The observed Cmax for the iris-ciliary body was observed after the Cmax for the sclera. The n-oxide of roflumilast was only observed within the analytical detection limits in the plasma and not in any components of the eye.

Figure 5:
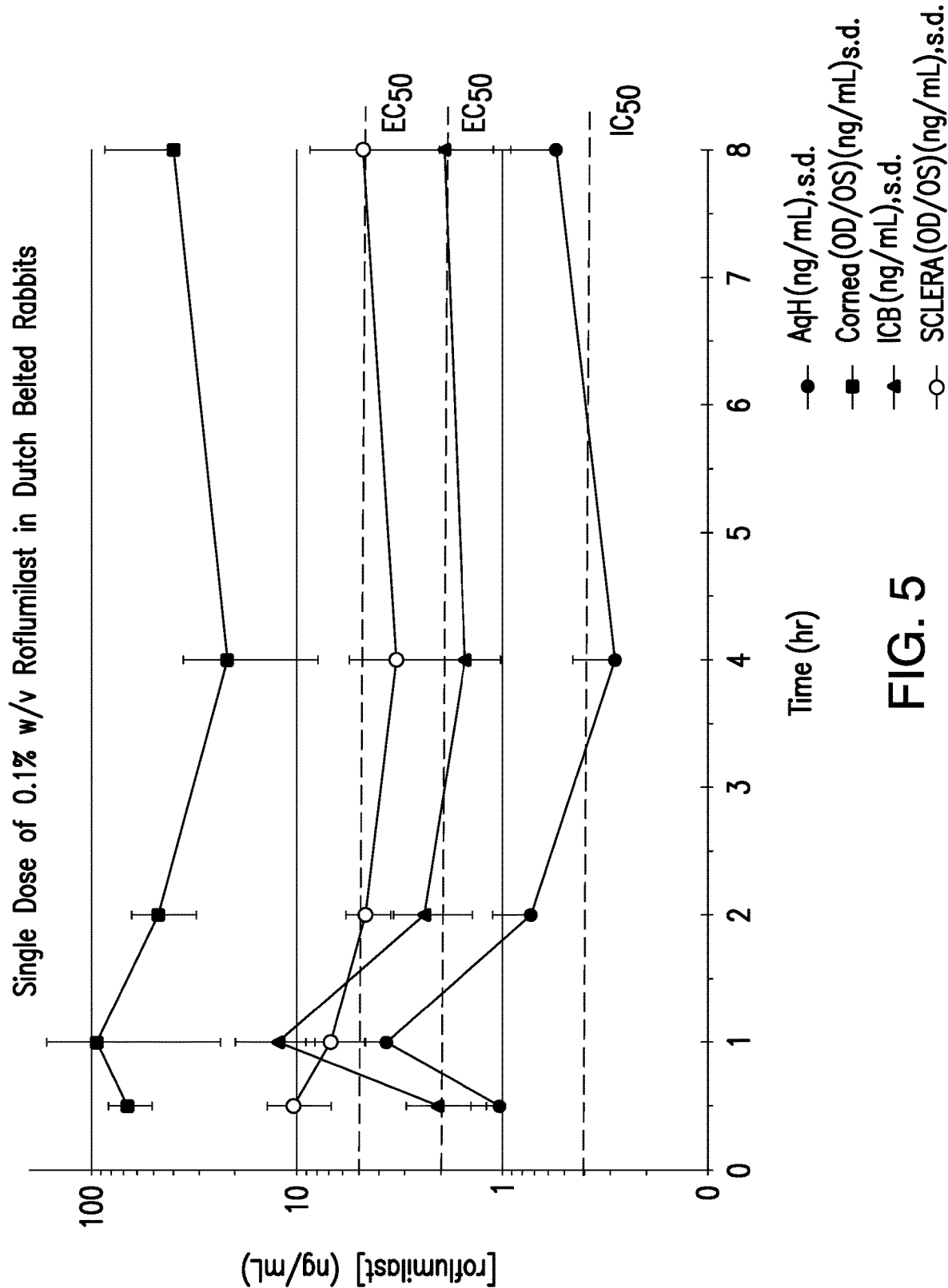
FIG. 5 is a graph depicting the concentration of roflumilast in various components of the eye following a single 25 µL dose of a 0.1% w/v suspension of roflumilast in Healthy Dutch Belted Rabbits. The x-axis is time in hours, and the y-axis is concentration (ng/mL) of roflumilast.

FIG. 5 is a graph depicting the concentration of roflumilast in the aqueous humor, cornea, iris-ciliary body, and sclera of the eye following a single 25 µL dose of a 0.1% w/v suspension of roflumilast. The x-axis is time in hours, and the y-axis is concentration (ng/mL) of roflumilast. FIG. 5 also illustrates the level of the drug relative to EC50 and IC50 levels of the corresponding drug and tissues, which indicate that the drug is present in various tissues of the eye in therapeutic amounts. One hour following administration, elevated levels of the drug were observed in the components of the eye. Surprisingly, there is a depot effect observed, wherein the level of drug increases several hours after administration relative to earlier time periods (e.g., 7-8 hours after administration of the drug). The relative levels of the drug in various components of the eye as illustrated in FIGS. 3-5, including low levels present in the lens, indicate that the drug is moving laterally through the eye even on day 1 of the study rather than directly traversing through the cornea through the aqueous humor to the lens.

Figure 6:
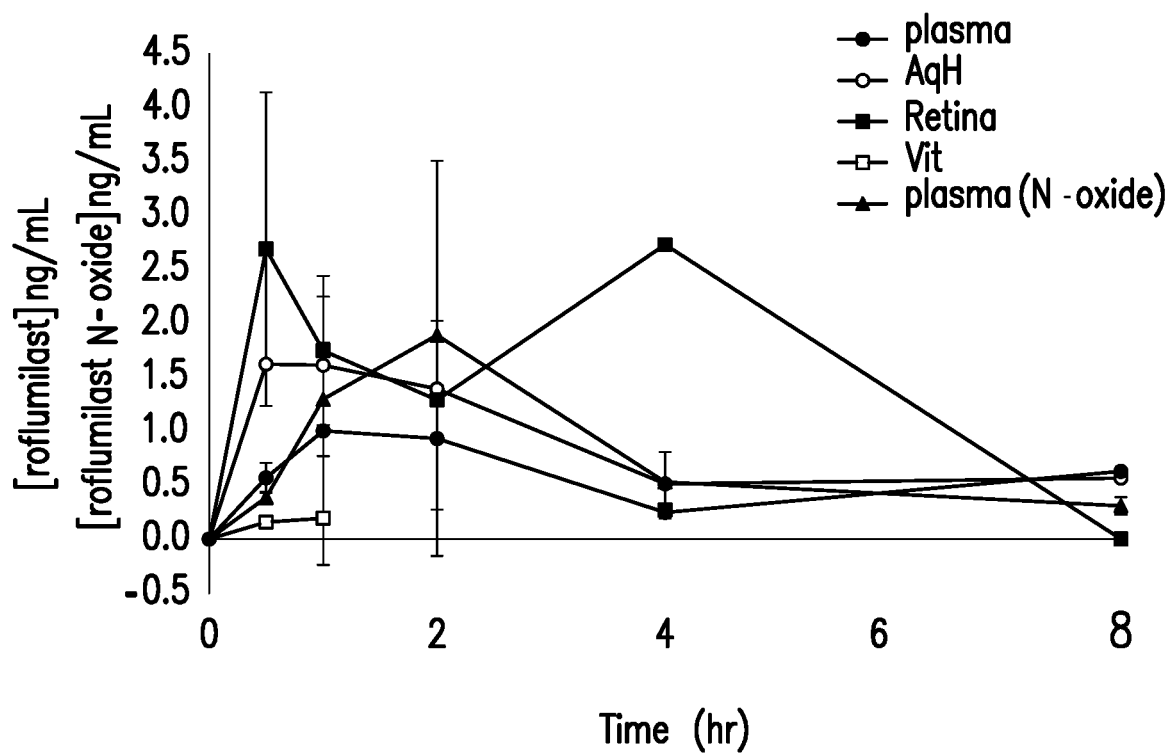
FIG. 6 is a graph depicting the concentration of roflumilast or roflumilast n-oxide in various components of the eye after five days administration (four days twice a day (BID), fifth day-single dose (QD)) of a 25 µL dose of a 0.1% w/v roflumilast dose in Healthy Dutch Belted Rabbits. The x-axis is time in hours, and the y-axis is concentration (ng/mL) of roflumilast or roflumilast n-oxide.
Figure 7:
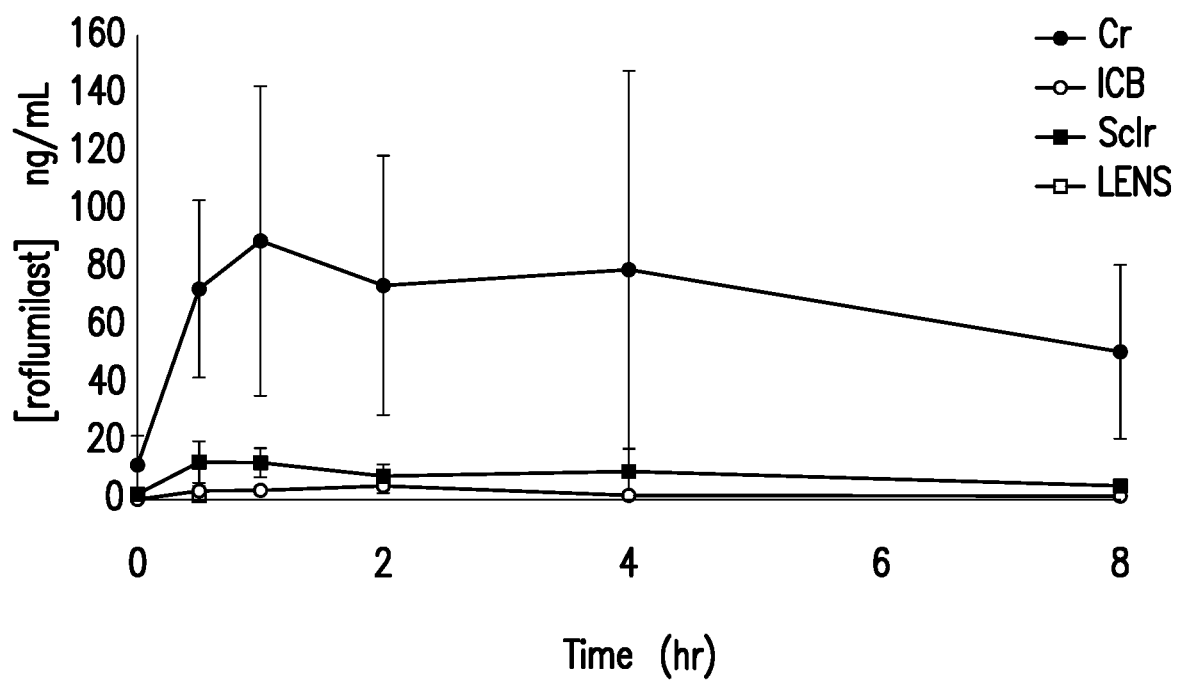
FIG. 7 is a graph depicting the concentration of roflumilast in various components of the eye after five days administration (four days twice a day (BID), fifth day-single dose (QD)) of a 25 µL dose of 0.1% w/v roflumilast dose in Healthy Dutch Belted Rabbits. The x-axis is time in hours, and the y-axis is concentration (ng/mL) of roflumilast.

FIGS. 6 and 7 show the concentration of roflumilast and roflumilast n-oxide (FIG. 6, only) in the plasma and various components of the eye on day 5 of the study after five days dosing of 25 µL dose of a 0.1% w/v roflumilast. FIG. 6 shows the concentration of roflumilast in the aqueous humor, retina-choroid plexus, and vitreous humor. FIG. 6 also shows the concentration of roflumilast n-oxide in the plasma. FIG. 7 shows the concentration of roflumilast in the cornea, iris-ciliary body, sclera, and lens (at 0.5 hours). In both FIGS. 6 and 7, the x-axis is time in hours, and the y-axis is concentration (ng/mL) of roflumilast or roflumilast n-oxide (FIG. 6, only).

FIGS. 6 and 7 show that there is high variability of the drug in the cornea and retina over time. The results indicate that there are non-zero levels of the drug in several components of the eye (e.g., the cornea and sclera) at the zero-time point on day 5. This observation indicates that there is drug still present in those components of the eye from prior days' administration of the drug. Further, this observation indicates that there is a corneal depot effect observed from the administration of roflumilast to the eye, from only a few days use. Again, surprisingly, the results indicate that the drug is reaching the ocular surface and anterior tissues of the eye, including for example, the cornea, the iris-ciliary body, the sclera, and the aqueous humor. Further, the result indicates that there is still exposure of the drug in the ocular surface and anterior of the eye from the administration of the drug on prior days. The concentration levels, for example in the cornea, also indicate that there is a steady state of the drug after five days of administration.

Figure 8:
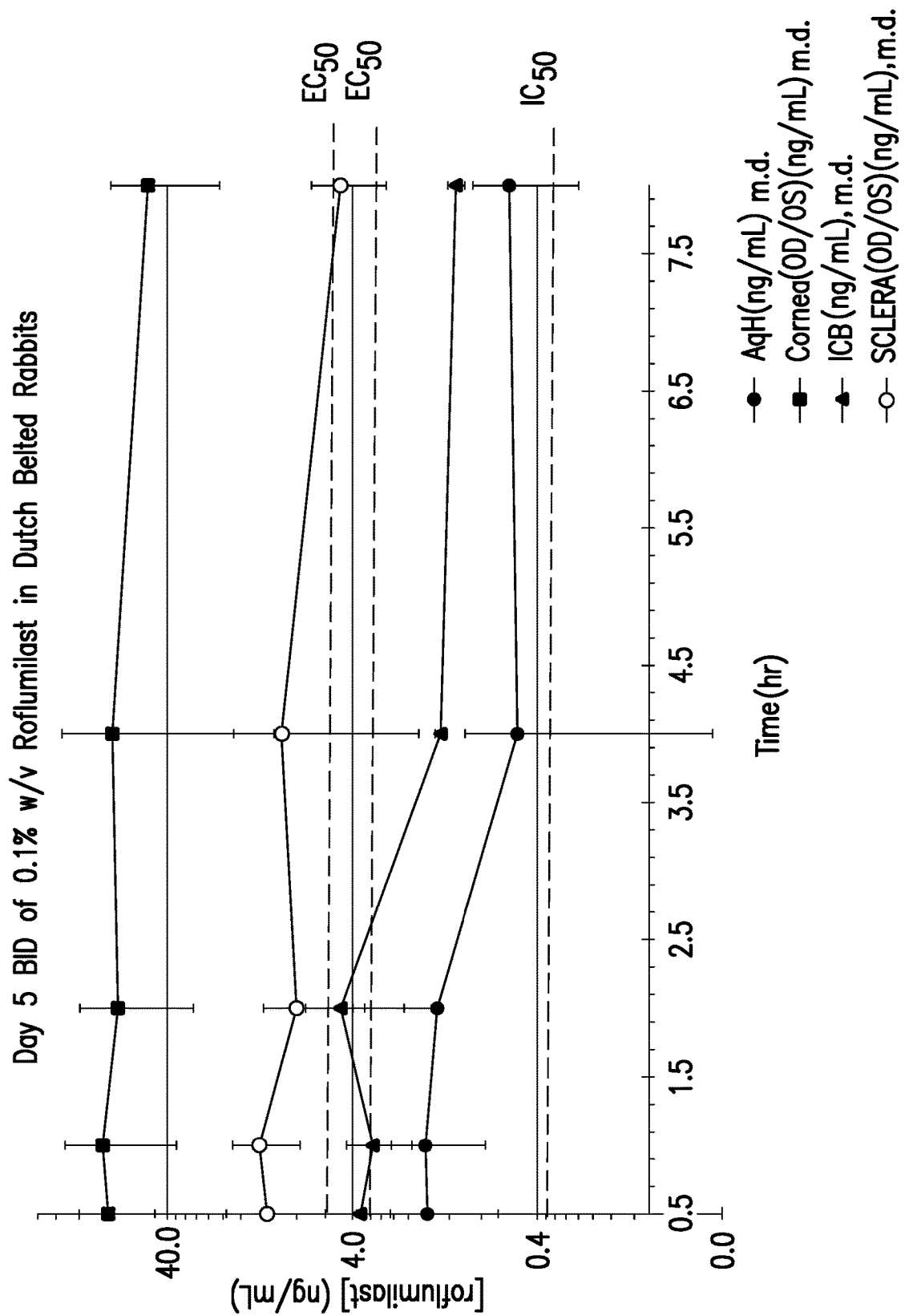
FIG. 8 is a graph depicting the concentration of roflumilast in various components of the eye on after five days administration (four days twice a day (BID), fifth day-single dose (QD)) of a 25 µL dose of a 0.1% w/v suspension of roflumilast in Healthy Dutch Belted Rabbits. The x-axis is time in hours, and the y-axis is concentration (ng/mL) of roflumilast.

FIG. 8 is a graph depicting the concentration of roflumilast in the aqueous humor, cornea, iris-ciliary body, and sclera of the eye after five days dosing of a 25 µL dose of a 0.1% w/v suspension of roflumilast. The x-axis is time in hours, and the y-axis is concentration (ng/mL) of roflumilast. FIG. 8 also illustrates the level of the drug relative to EC50 and IC50 levels of the drug relative to target tissues, which indicate that the drug is present in various tissues of the eye in therapeutic amounts. The concentration levels in the various components of the eye indicate that a steady state of drug concentration has been reached after five days of administration. The relative levels of the drug in various components of the eye as indicated in FIGS. 6-8, including low levels present in the lens, indicate that the drug is moving laterally through the eye at therapeutically relevant levels as proposed in FIG. 2.

Example 3

An ocular seven-day preclinical and pharmacokinetic study was conducted in mice. An ophthalmic suspension comprising 0.1% roflumilast was applied to both eyes of ten subjects twice per day for seven days as a test article for treatment of a model of immune-mediated allergic conjunctivitis initiated by both systemic and topical sensitization by ragweed. The suspension set forth in Table 2 was used for Example 3. Immediately following the final clinical intervention and final observation (30 minutes post final dose), animals were euthanized and both eyes were enucleated (OU) with optic nerve attached. The cornea, lens, conjunctiva, and eye cups from right eyes (OD) were collected, weighed, and snap frozen for bioanalysis. Up to 1 mL whole blood was collected immediately after euthanasia via cardiac puncture into K2EDTA tubes, kept on ice and then processed to plasma within 30 min by removing supernatant after 3000×g centrifugation. All samples were collected and prepared at approximately 2.5 hours following the last dose administration in the study. Roflumilast was detectable (lower limit of quantitation (LLOQ)=0.025 ng/mL) in plasma and tissues samples from animals treated with the ophthalmic suspension comprising 0.1% roflumilast (mean=1.5 ng/mL).

Figure 9:
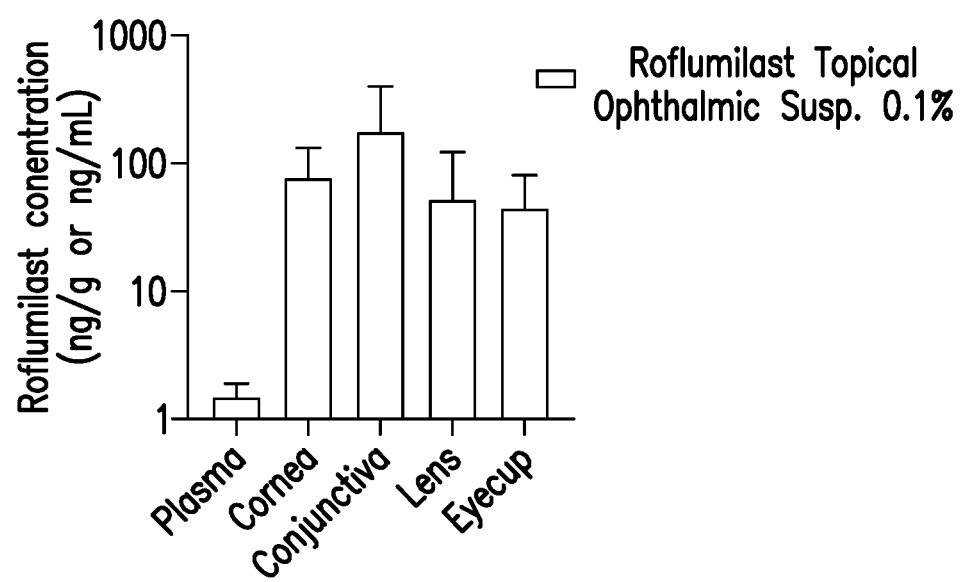
FIG. 9 is a graph depicting the concentration of roflumilast in various components of the eye in a murine model of inflammatory disease (female Balb/C mice with immune-induced allergic conjunctivitis via systemic and topical application of ragweed) after seven days of twice a day (BID) administration of a 3 µL dose a 0.1% w/v suspension of roflumilast from tissues taken within 2.5 h of the terminal dose. The x-axis reflects various components of the eye, and the y-axis is concentration (ng/g or ng/mL) of roflumilast.

The results of the study are set forth in FIG. 9. FIG. 9 shows the average concentration of roflumilast in the plasma and various components of the eye on day 7 of the study following the second of a twice a day dosing for seven days. FIG. 9 shows that there are elevated levels of roflumilast in the cornea and conjunctiva following administration. Surprisingly, the results indicate that the drug is reaching the ocular surface and anterior areas of the eye, including the cornea, confirming this result in a second species. Without being bound by theory, in this model of an active disease rather than in the study of healthy rabbits, additional permeability of ocular tissues may allow for higher ocular concentrations (adjusting for species anatomy and pharmacokinetic characteristics) in the anterior tissues such as lens. Scholz et al., "Pilocarpine permeability across ocular tissues and cell cultures: influence of formulation parameters," *J Ocul Pharmacol Ther.* 2002 October; 18(5):455-68; Kannan et al., "Impairment of conjunctival glutathione secretion and ion transport by oxidative stress in an adenovirus type 5 ocular infection model of pigmented rabbits," *Free Radic Biol Med.* 2004 Jul. 15; 37(2):229-38.

Example 4

Additional pharmaceutical compositions comprising roflumilast suitable for use with the disclosed methods were prepared. The ophthalmic pharmaceutical compositions comprising roflumilast set forth in Table 3, Table 4, Table 5, Table 6, and Table 7 were prepared.

TABLE 3

Ophthalmic Pharmaceutical Suspension of Roflumilast

| Ingredient | % w/v |
| --- | --- |
| Roflumilast | 0.1% w/v |
| Hydroxypropyl methylcellulose | 0.3% w/v |

TABLE 3-continued

Ophthalmic Pharmaceutical Suspension of Roflumilast

| Ingredient | % w/v |
| --- | --- |
| Polysorbate 80 | 0.1% w/v |
| Phosphate/Citrate Buffer | 0.45%/0.05% |
| Water for injection | q.s. ad 1.0 mL |

TABLE 4

Ophthalmic Pharmaceutical Suspension of Roflumilast

| Ingredient | % w/v |
| --- | --- |
| Roflumilast | 0.1% w/v |
| Hydroxyethyl cellulose | 0.35% w/v |
| Polysorbate 80 | 0.1% w/v |
| Phosphate/Citrate Buffer | 0.45%/0.05% |
| Water for injection | q.s. ad 1.0 mL |

TABLE 5

Ophthalmic Pharmaceutical Suspension of Roflumilast

| Ingredient | % w/v |
| --- | --- |
| Roflumilast | 0.1% w/v |
| Polyvinylpyrrolidone | 0.6% w/v |
| Tyloxapol | 0.3% w/v |
| Phosphate/Citrate Buffer | 0.45%/0.05% |
| Water for injection | q.s. ad 1.0 mL |

TABLE 6

Ophthalmic Pharmaceutical Suspension of Roflumilast

| Ingredient | % w/v |
| --- | --- |
| Roflumilast | 0.1% w/v |
| Carboxymethyl cellulose | 0.5% w/v |
| Polysorbate 80 | 0.1% w/v |
| Phosphate/Citrate Buffer | 0.45%/0.05% |
| Water for injection | q.s. ad 1.0 mL |

TABLE 7

Ophthalmic Pharmaceutical Ointment of Roflumilast

| Ingredient | Ointment #1 (% w/w) | Ointment #2 (% w/w) |
| --- | --- | --- |
| Roflumilast | 0.1% w/w | 1% w/w |
| Mineral oil | 20.2% w/w | 20% w/w |
| Petrolatum | 79.7% w/w | 79% w/w |

Example 5

An ocular five-day pharmacokinetic preclinical study was conducted in Healthy Dutch Belted Rabbits with three different groups (Group 1: n=21, Table 7 formulation; Group 2: n=21, Table 5 formulation; and Group 3: n=21 Table 3 formulation). Each of the groups was administered BID dosing of 40 uL of the ophthalmic suspension or ointment set forth in Table 7 (Group 1), Table 5 (Group 2), or Table 3 (Group 3) for four days and QD on the fifth day. Plasma concentrations of roflumilast and roflumilast n-oxide were measured at certain intervals following the terminal dose.

Additionally, the concentration of roflumilast in the cornea and conjunctiva was measured at various time points following the terminal dose.

Figure 10:
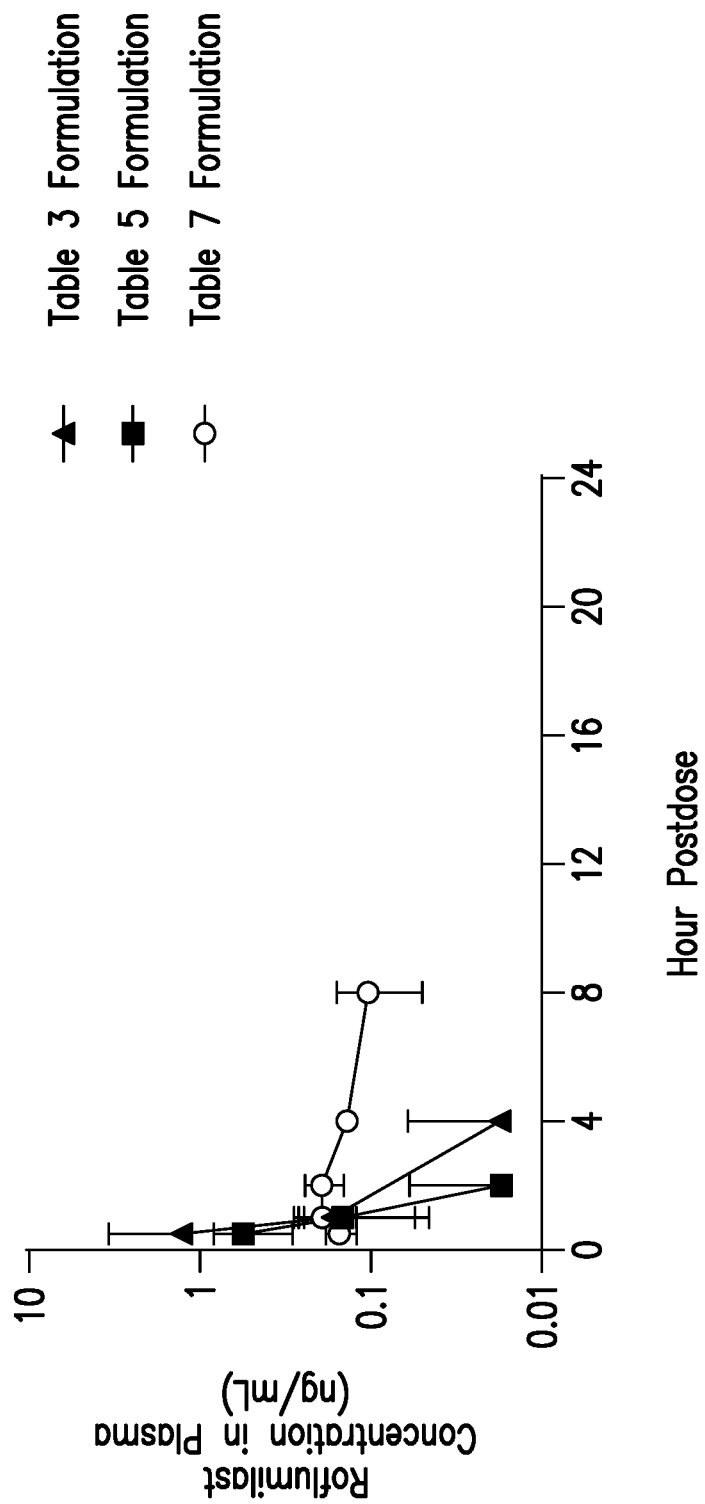
FIG. 10 is a graph depicting the concentration of roflumilast in the plasma after five days administration (four days twice a day (BID), fifth day-single dose (QD)) of three different ophthalmic compositions of a 40 µL dose of a 0.1% w/v roflumilast dose in Healthy Dutch Belted Rabbits. The x-axis is time in hours, and the y-axis is concentration (ng/mL) of roflumilast.
Figure 11:
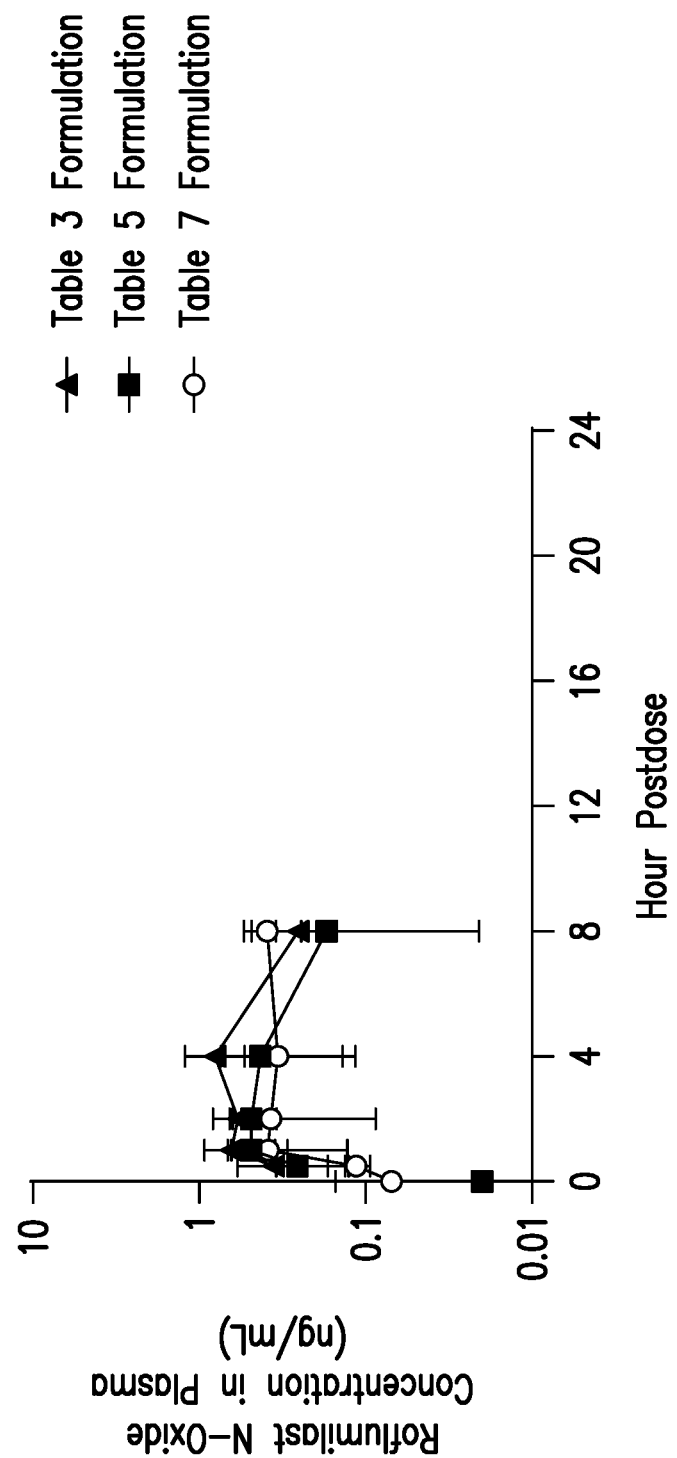
FIG. 11 is a graph depicting the concentration of roflumilast n-oxide in the plasma after five days administration (four days twice a day (BID), fifth day-single dose (QD)) of three different ophthalmic compositions of a 40 µL dose of a 0.1% w/v roflumilast dose in Healthy Dutch Belted Rabbits. The x-axis is time in hours, and the y-axis is concentration (ng/mL) of roflumilast n-oxide.
Figure 12:
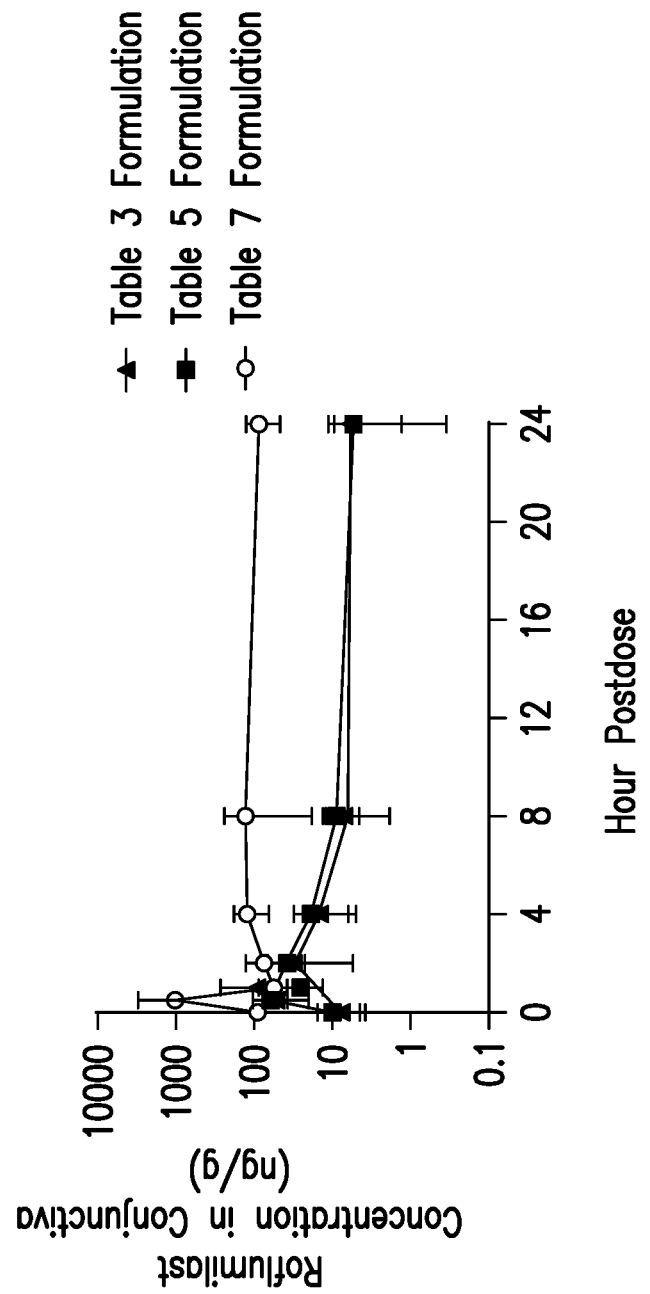
FIG. 12 is a graph depicting the concentration of roflumilast in the conjunctiva after five days administration (four days twice a day (BID), fifth day-single dose (QD)) of three different ophthalmic compositions of a 40 µL dose of a 0.1% w/v roflumilast dose in Healthy Dutch Belted Rabbits. The x-axis is time in hours, and the y-axis is concentration (ng/mL) of roflumilast.

The results of the study in Dutch Belted Rabbits are set forth in FIGS. 10-13. FIGS. 10 and 11 show the concentration of roflumilast and roflumilast n-oxide in the plasma after BID dosing for four days and QD dosing on the fifth day. FIG. 10 shows the concentration of roflumilast in the plasma 0, 0.5, 1, 2, 4, 8, and 24 hours after the terminal dose for each group. FIG. 11 shows the concentration of roflumilast n-oxide in the plasma 0, 0.5, 1, 2, 4, 8, and 24 hours after the terminal dose for each group. FIG. 12 shows the concentration of roflumilast in the conjunctiva 0, 0.5, 1, 2, 4, 8, and 24 hours after the terminal dose for each group. FIG. 13 shows the concentration of roflumilast in the cornea 0, 0.5, 1, 2, 4, 8, and 24 hours after the terminal dose for each group. In FIGS. 10-13, the x-axis is time in hours, and the y-axis is concentration (ng/mL) of roflumilast or roflumilast n-oxide. FIGS. 10-13 show that these additional formulations produced elevated levels of roflumilast in the cornea and conjunctiva following administration. Again, surprisingly, the results indicate that the drug is reaching the ocular surface and anterior areas of the eye, including the cornea and conjunctiva in therapeutic levels.

FIG. 10 is a graph depicting the concentration of roflumilast in the plasma after five days dosing of a 40 µL dose of three separate formulations of a 0.1% w/v of roflumilast, with twice a day (BID) dosing for four days, followed by one dose on day 5. The x-axis is time in hours, and the y-axis is concentration (ng/mL) of roflumilast. The concentration levels in the plasma indicate a decreasing drug concentration in plasma after terminal administration, those hours with data not shown were BLQ.

FIG. 11 is a graph depicting the concentration of roflumilast n-oxide in the plasma after five days dosing of a 40 µL dose of three separate formulations of a 0.1% w/v of roflumilast, with twice a day (BID) dosing for four days, followed by one dose on day 5. The x-axis is time in hours, and the y-axis is concentration (ng/mL) of roflumilast. The concentration levels in the plasma indicate a decreasing drug concentration in plasma after terminal administration, those hours with data not shown were BLQ.

FIG. 12 is a graph depicting the concentration of roflumilast in the conjunctiva after five days dosing of a 40 µL dose of three separate formulations of a 0.1% w/v of roflumilast, with twice a day (BID) dosing for four days, followed by one dose on day 5. The x-axis is time in hours, and the y-axis is concentration (ng/mL) of roflumilast. Each time point reflects n=6 eyes. The concentration levels in the conjunctiva indicate a steady state drug concentration has been reached with a value greater than 5ng/g pre-dose at 0 hours in the Table 3 and Table 5 formulations, and greater than 90ng/g in the Table 7 formulation, holding steady over the course of 24 hours. The larger surface area of the conjunctiva and its heterogeneity can contribute to the depot of suspension particles in the ocular surface.

FIG. 13 is a graph depicting the concentration of roflumilast in the cornea after five days dosing of a 40 µL dose of three separate formulations of a 0.1% w/v of roflumilast, with twice a day (BID) dosing for four days, followed by one dose on day 5. The x-axis is time in hours, and the y-axis is concentration (ng/mL) of roflumilast. Each time point reflects n=6 eyes. The concentration levels in the cornea indicate a steady state drug concentration has been reached with a value well at or above 35 ng/g pre-dose at 0 hours in the Table 3, 5, and 7 formulations, and holding a steady and high value over the course of 24 hours.

The foregoing description has been presented for purposes of illustration and description. This description is not intended to limit the invention to the precise form disclosed. Persons of ordinary skill in the art will appreciate that modifications and substitutions of the basic inventive description may be made.

What is claimed is:

1. A method for treating a patient having an inflammatory disorder of an ocular surface or anterior tissue of the eye, comprising:
   administering an ophthalmic pharmaceutical composition comprising a therapeutically effective amount of roflumilast to a cornea of said patient,
   wherein the ophthalmic pharmaceutical composition comprises ingredients set forth in Tables 1, 2, 3, 4, 5, or 6:

TABLE 1

| Ingredient | % w/v |
|---|---|
| Roflumilast | 0.10% w/v |
| Tyloxapol | 0.05% w/v |
| Carbopol 974B (Lubrizol) | 0.2% w/v |
| Glycerin | 2.0% w/v |
| Sodium chloride | 0.05% w/v |
| Water for injection | q.s. ad 1.0 mL |

TABLE 2

| Ingredient | % w/v |
|---|---|
| Roflumilast | 0.10% w/v |
| Tyloxapol | 0.05% w/v |
| Carbopol 974B (Lubrizol) | 0.25% w/v |
| Propylene glycol | 1.4 w/v % |
| Sodium chloride | 0.3% w/v |
| Mannitol | 0.3% w/v |
| Water for injection | q.s. ad 1.0 mL |

TABLE 3

| Ingredient | % w/v |
|---|---|
| Roflumilast | 0.1% w/v |
| Hydroxypropyl methylcellulose | 0.3% w/v |
| Polysorbate 80 | 0.1% w/v |
| Phosphate/Citrate Buffer | 0.45%/0.05% |
| Water for injection | q.s. ad 1.0 mL |

TABLE 4

| Ingredient | % w/v |
|---|---|
| Roflumilast | 0.1% w/v |
| Hydroxyethyl cellulose | 0.35% w/v |
| Polysorbate 80 | 0.1% w/v |
| Phosphate/Citrate Buffer | 0.45%/0.05% |
| Water for injection | q.s. ad 1.0 mL |

TABLE 5

| Ingredient | % w/v |
|---|---|
| Roflumilast | 0.1% w/v |
| Polyvinylpyrrolidone | 0.6% w/v |
| Tyloxapol | 0.3% w/v |

TABLE 5-continued

| Ingredient | % w/v |
| --- | --- |
| Phosphate/Citrate Buffer | 0.45%/0.05% |
| Water for injection | q.s. ad 1.0 mL |

TABLE 6

| Ingredient | % w/v |
| --- | --- |
| Roflumilast | 0.1% w/v |
| Carboxymethyl cellulose | 0.5% w/v |
| Polysorbate 80 | 0.1% w/v |
| Phosphate/Citrate Buffer | 0.45%/0.05% |
| Water for injection | q.s. ad 1.0 mL | wherein the composition delivers roflumilast to the cornea of said patient and subsequently travels laterally through the ocular surface and anterior tissues of the eye, and wherein the ophthalmic pharmaceutical composition is a suspension.

2. The method of claim 1, wherein said administration produces elevated levels of roflumilast in the cornea of the eye of the patient relative to a lens of the eye of the patient.

3. The method of claim 1, wherein said administration produces elevated levels of roflumilast in the cornea, the sclera, the iris-ciliary body, the conjunctiva, and the aqueous humor of the eye of the patient relative to a posterior tissue of the eye of the patient.

4. The method of claim 1, wherein said administration produces a depot effect in the cornea of the patient characterized by an increase in the concentration of roflumilast in the cornea relative to the concentration of roflumilast in the cornea at an earlier time period following administration.

5. The method of claim 1, wherein said administration produces a depot effect in an iris-ciliary body of the patient characterized by an increase in the concentration of roflumilast in the iris-ciliary body relative to the concentration of roflumilast in the iris-ciliary body at an earlier time period following administration.

6. The method of claim 1, wherein said administration produces a depot effect in a sclera of the patient characterized by an increase in the concentration of roflumilast in the sclera relative to the concentration of roflumilast in the sclera at an earlier time period following administration.

7. A method for treating a patient having an inflammatory disorder of an ocular surface or anterior tissue of the eye, comprising:
   administering an ophthalmic pharmaceutical composition comprising a therapeutically effective amount of roflumilast to a cornea of said patient,
   wherein the ophthalmic pharmaceutical composition comprises ingredients set forth in Tables 1, 2, 3, 4, 5, or 6:

TABLE 1

| Ingredient | % w/v |
| --- | --- |
| Roflumilast | 0.10% w/v |
| Tyloxapol | 0.05% w/v |
| Carbopol 974B (Lubrizol) | 0.2% w/v |
| Glycerin | 2.0% w/v |
| Sodium chloride | 0.05% w/v |
| Water for injection | q.s. ad 1.0 mL |

TABLE 2

| Ingredient | % w/v |
| --- | --- |
| Roflumilast | 0.10% w/v |
| Tyloxapol | 0.05% w/v |
| Carbopol 974B (Lubrizol) | 0.25% w/v |
| Propylene glycol | 1.4 w/v % |
| Sodium chloride | 0.3% w/v |
| Mannitol | 0.3% w/v |
| Water for injection | q.s. ad 1.0 mL |

TABLE 3

| Ingredient | % w/v |
| --- | --- |
| Roflumilast | 0.1% w/v |
| Hydroxypropyl methylcellulose | 0.3% w/v |
| Polysorbate 80 | 0.1% w/v |
| Phosphate/Citrate Buffer | 0.45%/0.05% |
| Water for injection | q.s. ad 1.0 mL |

TABLE 4

| Ingredient | % w/v |
| --- | --- |
| Roflumilast | 0.1% w/v |
| Hydroxyethyl cellulose | 0.35% w/v |
| Polysorbate 80 | 0.1% w/v |
| Phosphate/Citrate Buffer | 0.45%/0.05% |
| Water for injection | q.s. ad 1.0 mL |

TABLE 5

| Ingredient | % w/v |
| --- | --- |
| Roflumilast | 0.1% w/v |
| Polyvinylpyrrolidone | 0.6% w/v |
| Tyloxapol | 0.3% w/v |
| Phosphate/Citrate Buffer | 0.45%/0.05% |
| Water for injection | q.s. ad 1.0 mL |

TABLE 6

| Ingredient | % w/v |
| --- | --- |
| Roflumilast | 0.1% w/v |
| Carboxymethyl cellulose | 0.5% w/v |
| Polysorbate 80 | 0.1% w/v |
| Phosphate/Citrate Buffer | 0.45%/0.05% |
| Water for injection | q.s. ad 1.0 mL | wherein the composition delivers elevated levels of roflumilast to the ocular surface or an anterior portion of the eye of the patient relative to a posterior compartment of the eye of the patient, and wherein the ophthalmic pharmaceutical composition is a suspension.

8. The method of claim 7, wherein the ocular surface or anterior portion of the eye is a cornea.

9. The method of claim 7, wherein the ocular surface or anterior portion of the eye is a sclera.

10. The method of claim 7, wherein the ocular surface or anterior portion of the eye is an iris-ciliary body.

11. The method of claim 7, wherein the ocular surface or anterior portion of the eye is an aqueous humor.

12. The method of claim 7, wherein the ocular surface or anterior portion of the eye is a conjunctiva.

13. The method of claim 8, wherein said administration produces a depot effect in the cornea of the patient characterized by an increase in the concentration of roflumilast in the cornea relative to the concentration of roflumilast in the cornea at an earlier time period following administration.

14. The method of claim 10, wherein said administration produces a depot effect in an iris-ciliary body of the patient characterized by an increase in the concentration of roflumilast in the iris ciliary body relative to the concentration of roflumilast in the iris-ciliary body at an earlier time period.

15. The method of claim 9, wherein said administration produces a depot effect in a sclera of the patient characterized by an increase in the concentration of roflumilast in the sclera relative to the concentration of roflumilast in the sclera at an earlier time period following administration.

16. The method of claim 1, wherein the ophthalmic pharmaceutical composition has a pH between 6.0 and 8.0.

17. The method of claim 7, wherein the ophthalmic pharmaceutical composition has a pH between 6.0 and 8.0.

18. The method of claim 12, wherein said administration produces a depot effect in a conjunctiva of the patient characterized by an increase in the concentration of roflumilast in the conjunctiva relative to the concentration of roflumilast in the conjunctiva at an earlier time period following administration.

* * * * *